US012629324B2

(12) United States Patent
Friedrich et al.

(10) Patent No.: US 12,629,324 B2
(45) Date of Patent: May 19, 2026

(54) AQUEOUS COMPOSITIONS COMPRISING 6-UNDECANOL-ESTERS

(71) Applicant: Evonik Operations GmbH, Essen (DE)

(72) Inventors: Achim Friedrich, Hattingen (DE); Christian Hartung, Essen (DE); Jan Marian von Hof, Bochum (DE); Sven Klare, Cologne (DE)

(73) Assignee: Evonik Operations GmbH, Essen (DE)

( * ) Notice: Subject to any disclaimer, the term of this patent is extended or adjusted under 35 U.S.C. 154(b) by 378 days.

(21) Appl. No.: 18/546,509

(22) PCT Filed: Feb. 9, 2022

(86) PCT No.: PCT/EP2022/053067
§ 371 (c)(1),
(2) Date: Aug. 15, 2023

(87) PCT Pub. No.: WO2022/175141
PCT Pub. Date: Aug. 25, 2022

(65) Prior Publication Data
US 2024/0122831 A1      Apr. 18, 2024

(30) Foreign Application Priority Data

Feb. 17, 2021    (EP) ..................................... 21157569

(51) Int. Cl.
*A61K 8/37* (2006.01)
*A61Q 19/00* (2006.01)
*C12P 7/62* (2022.01)

(52) U.S. Cl.
CPC .............. *A61K 8/37* (2013.01); *A61Q 19/007* (2013.01); *C12P 7/62* (2013.01)

(58) Field of Classification Search
CPC ...................................................... A61K 8/37
See application file for complete search history.

(56) References Cited

U.S. PATENT DOCUMENTS

| | | | |
|---|---|---|---|
| 6,265,618 | B1 | 7/2001 | Zoeller et al. |
| 8,466,248 | B2 | 6/2013 | Meyer et al. |
| 9,072,917 | B2 | 7/2015 | Kawa et al. |
| 9,314,414 | B2 | 4/2016 | Dierker et al. |
| 2004/0242831 | A1 | 12/2004 | Tian et al. |
| 2007/0275447 | A1 | 11/2007 | Lewis et al. |
| 2008/0057554 | A1 | 3/2008 | Huhnke et al. |
| 2023/0023141 | A1 | 1/2023 | Von Hof et al. |
| 2023/0033620 | A1 | 2/2023 | Liebig et al. |
| 2023/0055814 | A1 | 2/2023 | Von Hof et al. |

FOREIGN PATENT DOCUMENTS

| | | |
|---|---|---|
| CN | 1241938 A | 1/2000 |
| CN | 109843388 A | 6/2019 |
| DE | 10 2008 001 788 | 11/2009 |
| EP | 1 731 498 | 12/2006 |
| WO | 98/00558 | 1/1998 |
| WO | 00/68407 | 11/2000 |
| WO | 2006/097235 | 9/2006 |
| WO | 2011/000489 | 1/2011 |
| WO | 2015/126624 A1 | 8/2015 |
| WO | 2022/263149 | 12/2022 |
| WO | 2022/263150 | 12/2022 |

OTHER PUBLICATIONS

Alonso et al., "Hydrogen-transfer reduction of carbonyl compounds promoted by nickel nanoparticles", Tetrahedron, vol. 64, 2008, pp. 1847-1852.
Altschul et al., "Basic Local Alignment Search Tool", J. Mol. Biol., vol. 215, 1990, pp. 403-410.
Chen et al., "Highly Chemoselective Catalytic Hydrogenation of Unsaturated Ketones and Aldehydes to Unsaturated Alcohols Using Phosphine-Stabilized Copper(I) Hydride Complexes", Tetrahedron, vol. 56, 2000, pp. 2153-2166.
Corma et al., "Conversion of levulinic acid derived valeric acid into a liquid transportation fuel of the kerosene type", Journal of Molecular Catalyst A: Chemical, vol. 388-389, 2014, pp. 116-122.
Devereux et al., "A comprehensive set of sequence analysis programs for the VAX", Nucleic Acids Research, vol. 12 No. 1, 1984, pp. 387-395.
Extended European Search Report received for European Patent Application No. 21157569.1, mailed on Jul. 29, 2021, 9 pages.
K. Schrader, "Grundlagen und Rezepturen der Kosmetika [Fundamentals and principles of cosmetics]", 2nd edition, Huthig Buch Verlag Heidelberg, 1989, pp. 329 to 341.
Gliński et al., "Catalytic Ketonisation Over Oxide Catalysts. Part IX. Single Step Synthesis of Aliphatic Saturated and Unsaturated $C_{11}$13 $C_{13}$ Ketones from Carboxylic Acids", Polish J. Chem., vol. 78, 2004, pp. 299-302.
Gorgas et al., "Efficient Hydrogenation of Ketones and Aldehydes Catalyzed by Well-Defined Iron(II) PNP Pincer Complexes: Evidence for an Insertion Mechanism", Organometallics, vol. 33, 2014, pp. 6905-6914.
Jadhav et al., "Production of Biomass-Based Automotive Lubricants by Reductive Etherification", ChemSusChem, vol. 10, 2017, pp. 2527-2533.
Lee et al., "A Practical and Cost-Effective Synthesis of D-erythro-Sphingosine from D-ribo-Phytosphingosine via a Cyclic Sulfate Intermediate", Synthesis, vol. 6, 2011, pp. 867-872.
Lee et al.," Ketonization of Hexanoic Acid to diesel-blendable 6-undecanone on the stable zirconia aerogel catalyst", Applied Catalysis A: General 506, 2015, pp. 288-293.

(Continued)

*Primary Examiner* — Shawquia Jackson
(74) *Attorney, Agent, or Firm* — Grüneberg Global IP, PLLC

(57)        ABSTRACT

Aqueous compositions containing 6-undecanol-esters are useful in cosmetic applications. Methods for producing 6-undecanol-esters are also provided.

20 Claims, 1 Drawing Sheet

(56)        References Cited

OTHER PUBLICATIONS

Morinaga et al., "The production of acetic acid from carbon dioxide and hydrogen by an anaerobic bacterium", Journal of Biotechnology, vol. 14, 1990, pp. 187-194.

Needleman et al., "A General Method Applicable to the Search for Similarities in the Amino Acid Sequence of Two Proteins", J. Mol. Biol, vol. 48, 1970, pp. 443-453.

Orozco et al., "Carbon-Carbon Bond Formation and Hydrogen Production in the Ketonization of Aldehydes", ChemSumChem, vol. 9, 2016, pp. 2430-2442.

Orozco et al., "Cerium Oxide as Catalyst for the Ketozination of Aldehydes: Mechanistic insights and a Convenient way to Alkanes without Consumption of External Hydrogen", Green Chemistry, vol. 19, No. 6, 2017, pp. 1555-1569.

Pham et al., "Ketonization of Carboxylic Acids: Mechanisms, Catalysts, and Implications for Biomass Conversion", ACS Catalysis, vol. 3, 2013, pp. 2456-2473.

Sakai et al., "Ethanol Production from $H_2$ and $CO_2$ by a newly isolated thermophilic bacterium, *Moorella* sp. HUC22-1", Biotechnology Letters, vol. 26, 2004, pp. 1607-1612.

Schmidt et al., "Production of Acetic acid from hydrogen and carbon dioxide by clostridium species ATCC 29797", Chem. Eng. Commun., vol. 45, 1986, pp. 61-73.

Shah et al., "Selective Heterogenous Catalytic Hydrogenation of Ketone (C=O) to Alcohol (OH) by Magnetite Nanoparticles Following Langmuir-Hinshelwood Kinetic Approach", ACS Appl. Mater. Interfaces., vol. 7, 2015, pp. 6480-6489.

Wang et al., "Experimental and theoretical evidence for the reactivity of bound intermediates in ketonization of carboxylic acids and consequences of acid-base properties of oxide catalysts", J. Phys. Chem C, vol. 121, 2017, pp. 18030-18046.

Woo et al., " Role of Anhydride in the Ketonization of Carboxylic Acid: Kinetic Study on Dimerization of Hexanoic Acid", Ind. Eng. Chem. Res, vol. 56, 2017, pp. 872-880.

U.S. Appl. No. 17/757,576, filed Jun. 17, 2022, 2023/0055814, Von Hof et al.

U.S. Appl. No. 17/757,711, filed Jun. 17, 2022, 2023/0033620, Liebig et al.

U.S. Appl. No. 17/757,528, filed Jun. 16, 2022, 2023/0023141, Von Hof et al.

International Search Report dated May 18, 2022, in PCT/EP2022/053067, 4 pages.

Kostikov et al., "Synthesis of alkenes by elimination reactions", Science of synthesis, Georg Thieme Verlag KG, vol. 47b, (volume date 2009), 2010, pp. 771-881.

Written Opinion dated May 18, 2022, in PCT/EP2022/053067, 7 pages.

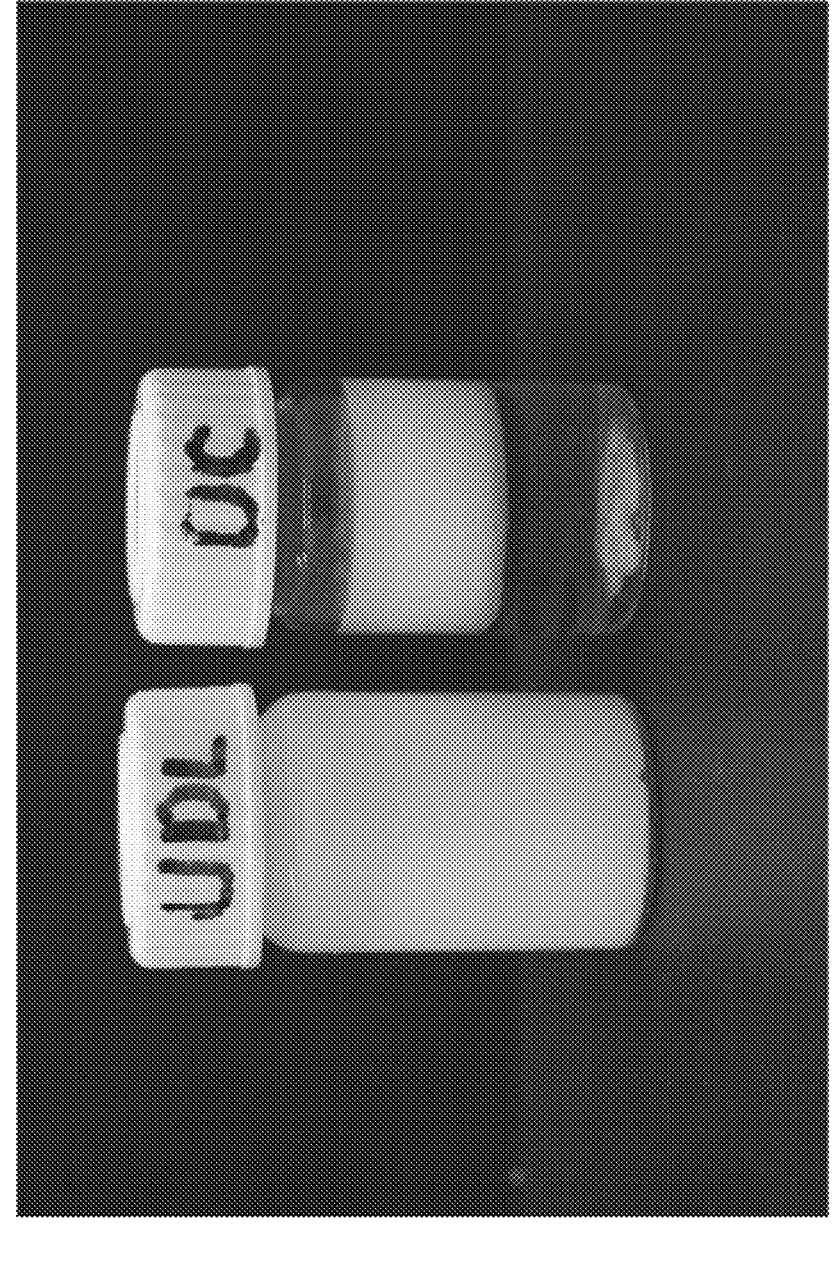

AQUEOUS COMPOSITIONS COMPRISING 6-UNDECANOL-ESTERS

CROSS-REFERENCE TO RELATED APPLICATIONS

This application is the National Stage entry under § 371 of International Application No. PCT/EP2022/053067, filed on Feb. 9, 2022, and which claims the benefit of priority to European Application No. 21157569.1, filed on Feb. 17, 2021. The content of each of these applications is hereby incorporated by reference in its entirety.

BACKGROUND OF THE INVENTION

Field of the Invention

The invention relates to aqueous compositions comprising 6-undecanol-esters and methods for producing 6-undecanol-esters, as well as the use of 6-undecanol-esters in cosmetic applications.

Description of Related Art

Cosmetic leave-on formulations such as sun protection formulations consist predominantly of an emulsion with a water and an oil phase. A wide variety of cosmetic oils are used for the oil phase. These can traditionally be, for example, petrochemically based mineral oils or other low-cost products based on mineral oils. In up-to-date formulations, however, an attempt is made to avoid petrochemical origin of formulation components as far as possible due to sustainability aspects. Fatty acid-fatty alcohol esters or vegetable and animal fats and waxes are therefore often used. Appropriately suitable oils fall within the range of medium-to-heavy oils with rather average application properties such as viscosities in the range of 10-50 mPas at room temperature and surface tensions in the range of 26-32 mN/m and associated medium to good spreading behavior and medium to low polarity. Apart from the cleansing and nourishing effects of such cosmetic formulations, which determine the application purpose, emphasis is placed on parameters as diverse as the highest possible dermatological compatibility, good refatting properties, elegant appearance, easy spreading, optimal sensory impression and storage stability.

In order to offer solutions with further improved CO2 footprint and ingredients of non-tropical origin, new solutions are identified. One promising option is to create cosmetic raw materials directly from CO2 as starting material. This opens the door to a new level of sustainable ingredients for cosmetic products matching the consumer need of true sustainable cosmetics.

SUMMARY OF THE INVENTION

The object of the invention was to provide an emollient for outstanding cosmetic use.

It was found that, surprisingly, 6-undecanol-esters have excellent properties for cosmetic applications.

It is an advantage of the instant invention, that the compositions containing at least one 6-undecanol-ester have excellent sensory properties on surfaces like skin and hair.

Another advantage of the instant invention is, that the compositions containing at least one 6-undecanol-ester have nearly no colour.

Another advantage of the instant invention is, that the compositions containing at least one 6-undecanol-ester are nearly odourless.

Another advantage of the instant invention is, that the compositions containing at least one 6-undecanol-ester show very good solubility for active substances.

Another advantage of the instant invention is, that the compositions containing at least one 6-undecanol-ester show very good spreading properties on the skin.

Another advantage of the instant invention is, that the compositions containing at least one 6-undecanol-ester have a high hydrolytic stability, especially at low pH and at higher and lower temperatures.

Another advantage of the instant invention is, that the compositions containing at least one 6-undecanol-ester show good moisturizing effects.

Another advantage of the instant invention is, that the compositions containing at least one 6-undecanol-ester show good wetting properties.

Another advantage of the instant invention is, that the compositions containing at least one 6-undecanol-ester are based on raw materials that are renewable to a high degree or even completely renewable.

Another advantage of the instant invention is, that the compositions containing at least one 6-undecanol-ester can be carbon (CO2) neutral.

Another advantage of the instant invention is, that the compositions containing at least one 6-undecanol-ester show good solubilization performance for organic UV filters.

Another advantage of the instant invention is, that the compositions containing at least one 6-undecanol-ester show a good toxicological profile.

Another advantage of the instant invention is, that the compositions containing at least one 6-undecanol-ester show less spreadability than comparable light emollients.

Another advantage of the instant invention is, that the compositions containing at least one 6-undecanol-ester show good pigment stabilization.

Another advantage of the instant invention is, that the compositions containing at least one 6-undecanol-ester show good freeze stability.

The present invention provides aqueous compositions containing at least one 6-undecanol-ester selected from 6-undecanol-esters obtainable by esterification of undecan-6-ol with one selected from A) monocarboxylic acids with 6 to 32, preferably 6 to 22, more preferably 8 to 22 carbon atoms, and B) polyfunctional carboxylic acids with 2 to 44, preferably 3 to 38, more preferably 4 to 18, carbon atoms, preferably tricarboxylic and dicarboxylic acids, more preferably dicarboxylic acids with 2 to 18, preferably 3 to 13, more preferably 4 to 11, carbon atoms.

BRIEF DESCRIPTION OF THE DRAWING

The FIGURE shows emulsions after repeated freezing/thawing.

DETAILED DESCRIPTION OF THE INVENTION

The term "6-undecanol-ester" is used as a synonym for "undec-6-yl ester" in context of the instant invention.

The term "aqueous" in context of the instant invention means compositions containing water in an amount of at least 2 wt.-%, preferably of at least 10 wt.-%, more preferably of at least 30 wt.-%, wherein the weight percentages refer to the total composition.

Within the context of the present invention, the term "polyfunctional carboxylic acid" is to be understood as meaning carboxylic acids which have more than one carboxyl group.

The "pH" in connection with the present invention is defined as the value which is measured for the corresponding substance at 25° C. after stirring for 5 minutes using a pH electrode calibrated in accordance with ISO 4319 (1977).

Unless stated otherwise, all percentages (%) given are percentages by mass.

Any kind of monocarboxylic acid can be used in the context of the instant invention, like for example saturated or unsaturated, linear or branched, substituted or unsubstituted monocarboxylic acids such as capronic acid, cyclopentane carboxylic acid, 2-methylpentanoic acid, heptanonic acid, cyclohexanecarboxylic acid, caprylic acid, 2-ethylhexanic acid, sorbic acid, isononaoic acid, 3,5,5-trimethylhexanoic acid, capric acid, pelargonic acid, 2-propylheptanoic acid, iso-decanoic acid, undecanoic acid, 11-undecylenic acid, 2-butyloctanoic acid, lauric acid, myristic acid, palmitic acid, palmitoleic acid, ricinolic acid, stearic acid, oleic acid, isostearic acid, 12-hydroxystearic acid, arachic acid, or behenic acid.

Preferred aqueous compositions according to the instant invention are characterized in, that the monocarboxylic acid is selected from fatty acids, preferably natural fatty acids. Natural fatty acids can be produced on the basis of naturally occurring vegetable or animal oils and have preferably 6-30 carbon atoms, especially 8-22 carbon atoms. Natural fatty acids are generally unbranched and consist of an even number of carbon atoms. Any double bonds have cis configuration. Examples are: caproic acid, caprylic acid, capric acid, lauric acid, myristic acid, palmitic acid, palmitoleic acid, isostearic acid, stearic acid, 12-hydroxystearic acid, dihydroxystearic acid, oleic acid, linoleic acid, linolenic acid, petroselic acid, elaidic acid, arachic acid, behenic acid, erucic acid, gadoleic acid, linolenic acid, eicosapentaenoic acid, docosahexaenoic acid, arachidonic acid.

More preferred aqueous compositions according to the instant invention are characterized in, that the monocarboxylic acid is selected from hexanoic acid, caprylic acid, pelargonic acid, capric acid, lauric acid, 11-undecylenic acid, myristic acid, palmitic acid, palmitoleic acid, ricinolic acid, stearic acid, 12-hydroxy-stearic acid, isostearic acid, oleic acid and behenic acid.

Any kind of polyfunctional acid can be used in the context of the instant invention, like, for example, di- and tricarboxylic acids, dimer fatty acids as specified in EP1683781, oxalic acid, fumaric acid, malonic acid, succinic acid, glutaric acid, adipic acid, pimelic acid, suberic acid, azelaic acid, sebacic acid, dodecanedioic acid, malic acid, tartaric acid, tartronic acid, maleic acid, citric acid, and also aromatic acids, like for example phthalic acid, isophthalic acid or terephthalic acid.

Preferred aqueous compositions according to the instant invention are characterized in, that the polyfunctional carboxylic acid is selected from aliphatic, linear dicarboxylic acids, in particular selected from oxalic acid, malonic acid, tartronic acid, succinic acid, maleic acid, tartaric acid, maleic acid, fumaric acid, sorbic acid, alpha-ketoglutaric acid, glutaric acid, adipic acid, pimelic acid, cork acid, azelaic acid, sebacic acid, undecane dicarboxylic acid, dodecane dicarboxylic acid and brassylic acid.

The aqueous compositions according to the invention preferably are formulations.

Within the context of the present invention, the term "formulation" is to be understood as meaning a composition which according to its intended use contains—next to water and the ester—at least one further component, which is obvious for a person skilled in the art for the formulation to be enabled to fulfil its intended use. For example, obviously a pharmaceutical formulation needs to contain at least one therapeutically active component to be considered "pharmaceutical", cosmetic formulations usually contain a cosmetically acceptable carrier.

Formulations according to the instant invention for example can be pharmaceutical, dermatological, personal care, cosmetic, household care, professional skin care and pet care formulations.

The aqueous compositions according to the invention preferably are cosmetic formulations.

Preferred formulations according to the invention comprise, in addition to water and the ester, at least one further component selected from the group of
emollients,
emulsifiers,
thickeners/viscosity        regulators/stabilizers/consistency
   enhancers,
UV light protection filters,
antioxidants,
humectants,
solids and fillers,
pigments,
film formers,
pearlescence/opacifiying additives,
deodorant and antiperspirant active ingredients,
insect repellents,
self-tanning agents,
perfumes,
preservatives,
propellants,
conditioners,
dyes,
cosmetic active ingredients,
care additives,
superfatting agents,
solvents,
wherein humectants, emollients, emulsifiers, stabilizers/consistency enhancers, perfumes, preservatives, UV light protection filters, pigments and cosmetic active ingredients are preferably comprised, with humectants, UV light protection filters and pigments being most preferred. Substances which can be used as exemplary representatives of the individual groups are known to the person skilled in the art and can be found for example in the German application DE 102008001788.4. This patent application is herewith incorporated as reference and thus forms part of the disclosure.

As regards further optional components and the amounts used of these components, reference is made expressly to the relevant handbooks known to the person skilled in the art, for example K. Schrader, "Grundlagen and Rezepturen der Kosmetika [Fundamentals and principles of cosmetics]", 2nd edition, pages 329 to 341, Hüthig Buch Verlag Heidelberg.

The amounts of the particular additives are governed by the intended use.

Typical guide formulations for the respective applications are known prior art and are contained for example in the brochures of the manufacturers of the particular basic materials and active ingredients. These existing formulations can usually be adopted unchanged. If necessary, the desired modifications can, however, be undertaken without complication by means of simple experiments for the purposes of adaptation and optimization.

Preferred humectants comprised in the formulations according to the instant invention are selected from the group of glycerol, 1,2-propylene glycol, 1,3-propanediol, diglycerol, dipropylene glycol, xylitol, sorbitol, maltitol, 1,2-butylene glycol, 1,3-butylene glycol, 1,2-pentylene glycol, 1,2-hexylene glycol, lactic acid, creatine and urea.

The 6-undecanol-esters comprised in the composition according to the instant invention can be prepared according to methods know in the art.

Advantageously and therefore preferred according to the instant invention, the 6-undecanol-esters comprised in the composition according to the instant invention are prepared by a method for preparing 6-undecanol-esters containing the steps (a) providing ethanol and/or a lower alkanoic acid or any salts thereof and contacting the aforementioned with at least one microorganism capable of carrying out two-carbon chain elongation to produce hexanoic acid and/or a salt thereof and/or an ester thereof;

(b) contacting the hexanoic acid and/or the salt thereof and/or the ester thereof from (a) with at least one ketonization catalyst under suitable reaction conditions for chemical ketonization of the hexanoic acid and/or the salt thereof and/or the ester thereof to 6-undecanone;

(c) contacting the 6-undecanone with at least one hydrogenation metal catalyst for catalytic hydrogenation of the 6-undecanone to 6-undecanol;

(d) esterification of the 6-undecanol with at least one selected from

A) acyl group donors providing acyl groups of the acids selected from monocarboxylic acids with 6 to 32, preferably 6 to 22, more preferably 8 to 22 carbon atoms, and B) acyl group donors providing acyl groups of the acids selected from polyfunctional carboxylic acids with 2 to 44, preferably 3 to 38, more preferably 4 to 18, carbon atoms, preferably tricarboxylic and dicarboxylic acids, more preferably dicarboxylic acids with 2 to 18, preferably 3 to 13, more preferably 4 to 11, carbon atoms.

The term "lower alkanoic acid" as used herein refers to an alkanoic acid comprising less than six carbon atoms. Examples for lower alkanoic acids are acetic acid (acetate), propanoic acid (propanoate), butanoic acid (butanoate) or pentanoic acid (pentanoate). The term "contacting", as used herein, means bringing about direct contact between the microorganism and the ethanol and/or the lower alkanoic acid, e.g. acetate. In one example, ethanol is the carbon source and the contacting in step (a) involves contacting the ethanol with the microorganism of step (a). The contact may be a direct contact or an indirect one that may include a membrane or the like separating the cells from the ethanol or where the cells and the ethanol may be kept in two different compartments etc.

The source of the ethanol and/or the lower alkanoic acid or any salts thereof provided in step (a) of the method according to the instant invention may vary depending on availability. For example, the ethanol and/or the lower alkanoic acid or any salts thereof is the product of fermentation of synthesis gas (syngas) or any carbohydrate known in the art. In particular, the carbon source for the production by microorganisms of the ethanol and/or the lower alkanoic acid or any salts thereof may be selected from the group consisting of alcohols, aldehydes, glucose, sucrose, fructose, dextrose, lactose, xylose, pentose, polyol, hexose, ethanol and synthesis gas. Mixtures of sources can be used as a carbon source.

Preferably, the carbon source is synthesis gas (syngas). The synthesis gas is preferably converted to the ethanol and/or the lower alkanoic acid or any salts thereof by at least one acetogenic microorganism.

With respect to the source of the syngas comprising carbon dioxide and/or carbon monoxide, a skilled person would understand that many possible sources for the provision of the syngas comprising CO and/or $CO_2$ as a carbon source exist. The syngas or sources of syngas may be derived for instance from steam reforming, partial oxidation or electrochemical synthesis from water or $CO_2$. It can be seen that in practice, as the carbon source for the production by microorganisms of the ethanol and/or the lower alkanoic acid or any salts thereof of the present invention any gas or any gas mixture can be used which is able to supply the microorganisms with sufficient amounts of carbon, so that the ethanol and/or the lower alkanoic acid or any salts thereof is formed from the source of CO and/or $CO_2$.

Generally, for the acetogenic microorganism of the present invention the carbon source comprises at least 50% by weight, at least 70% by weight, particularly at least 90% by weight of $CO_2$ and/or CO, wherein the percentages by weight-% relate to all carbon sources that are available to the cell according to any aspect of the present invention.

Examples of carbon sources in gas forms include exhaust gases such as synthesis gas, flue gas and petroleum refinery gases produced by yeast fermentation or clostridial fermentation. These exhaust gases are formed from the gasification of cellulose-containing materials or coal gasification. In one example, these exhaust gases may not necessarily be produced as by-products of other processes but can specifically be produced for use with the mixed culture of the present invention.

According to any aspect of the present invention, the carbon source for the production of the ethanol and/or the lower alkanoic acid or any salts thereof provided in step (a) of the method according to the instant invention is may be synthesis gas. Synthesis gas can for example be produced as a by-product of coal gasification. Accordingly, the microorganism according to any aspect of the present invention may be capable of converting a substance which is a waste product into a valuable resource.

In another example, the synthesis gas may be a by-product of gasification of widely available, low-cost agricultural raw materials.

There are numerous examples of raw materials that can be converted into synthesis gas, as almost all forms of vegetation can be used for this purpose. In particular, raw materials are selected from the group consisting of perennial grasses such as miscanthus, corn residues, processing waste such as sawdust and the like.

In general, synthesis gas may be obtained in a gasification apparatus of dried biomass, mainly through pyrolysis, partial oxidation and steam reforming, wherein the primary products of the synthesis gas are CO, $H_2$ and $CO_2$. Syngas may also be a product of electrolysis of $CO_2$. A skilled person would understand the suitable conditions to carry out electrolysis of $CO_2$ to produce syngas comprising CO in a desired amount.

Usually, a portion of the synthesis gas obtained from the gasification process is first processed in order to optimize product yields, and to avoid formation of tar. Cracking of the undesired tar and CO in the synthesis gas may be carried out using lime and/or dolomite.

The overall efficiency, ethanol and/or acetate productivity and/or overall carbon capture of the method of the present invention may be dependent on the stoichiometry of the $CO_2$, CO, and $H_2$ in the continuous gas flow. The continuous gas flows applied may be of composition $CO_2$ and $H_2$. In particular, in the continuous gas flow, concentration range of $CO_2$ may be about 10-50%, in particular 3% by weight and $H_2$ would be within 44% to 84%, in particular, 64 to 66.04% by weight. In another example, the continuous gas flow can also comprise inert gases like $N_2$, up to a $N_2$ concentration of 50% by weight.

More in particular, the carbon source comprising CO and/or $CO_2$ contacts the acetogenic microorganism in a continuous gas flow. Even more in particular, the continuous gas flow comprises synthesis gas. These gases may be supplied for example using nozzles that open up into the aqueous medium, frits, membranes within the pipe supplying the gas into the aqueous medium and the like.

A skilled person would understand that it may be necessary to monitor the composition and flow rates of the streams at relevant intervals. Control of the composition of the stream can be achieved by varying the proportions of the constituent streams to achieve a target or desirable composition. The composition and flow rate of the blended stream can be monitored by any means known in the art. In one example, the system is adapted to continuously monitor the flow rates and compositions of at least two streams and combine them to produce a single blended substrate stream in a continuous gas flow of optimal composition and means for passing the optimized substrate stream to the fermenter.

According to any aspect of the present invention, a reducing agent, for example hydrogen may be supplied together with the carbon source. In particular, this hydrogen may be supplied when the CO and/or $CO_2$ is supplied and/or used. In one example, the hydrogen gas is part of the synthesis gas present according to any aspect of the present invention. In another example, where the hydrogen gas in the synthesis gas is insufficient for the method of the present invention, additional hydrogen gas may be supplied.

The term "acetogenic microorganism" as used herein refers to a microorganism which is able to perform the Wood-Ljungdahl pathway and thus is able to convert CO, $CO_2$ and/or hydrogen to a lower alkanoic acid, e.g. acetate. These microorganisms include microorganisms which in their wild-type form do not have a Wood-Ljungdahl pathway, but have acquired this trait as a result of genetic modification. Such microorganisms include but are not limited to *E. coli* cells. These microorganisms may be also known as carboxydotrophic bacteria. Currently, 21 different genera of the acetogenic bacteria are known in the art (Drake et al., 2006), and these may also include some clostridia (Drake & Kusel, 2005). These bacteria are able to use carbon dioxide or carbon monoxide as a carbon source with hydrogen as an energy source (Wood, 1991). Further, alcohols, aldehydes, carboxylic acids as well as numerous hexoses may also be used as a carbon source (Drake et al., 2004). The reductive pathway that leads to the formation of acetate is referred to as acetyl-CoA or Wood-Ljungdahl pathway.

In particular, the acetogenic microorganism may be selected from the group consisting of *Acetoanaerobium notera* (ATCC 35199), *Acetonema longum* (DSM 6540), *Acetobacterium carbinolicum* (DSM 2925), *Acetobacterium malicum* (DSM 4132), *Acetobacterium* species no. 446 (Morinaga et al., 1990, *J. Biotechnol.*, Vol. 14, p. 187-194), *Acetobacterium wieringae* (DSM 1911), *Acetobacterium woodii* (DSM 1030), *Alkalibaculum bacchi* (DSM 22112), *Archaeoglobus fulgidus* (DSM 4304), *Blautia producta*

(DSM 2950, formerly *Ruminococcus productus*, formerly *Peptostreptococcus productus*), *Butyribacterium methylotrophicum* (DSM 3468), *Clostridium aceticum* (DSM 1496), *Clostridium autoethanogenum* (DSM 10061, DSM 19630 and DSM 23693), *Clostridium carboxidivorans* (DSM 15243), *Clostridium coskatii* (ATCC no. PTA-10522), *Clostridium drakei* (ATCC BA-623), *Clostridium formicoaceticum* (DSM 92), *Clostridium glycolicum* (DSM 1288), *Clostridium ljungdahlii* (DSM 13528), *Clostridium ljungdahlii* C-01 (ATCC 55988), *Clostridium ljungdahlii* ERI-2 (ATCC 55380), *Clostridium ljungdahlii* 0-52 (ATCC 55989), *Clostridium mayombei* (DSM 6539), *Clostridium methoxybenzovorans* (DSM 12182), *Clostridium ragsdalei* (DSM 15248), *Clostridium scatologenes* (DSM 757), *Clostridium* species ATCC 29797 (Schmidt et al., 1986, *Chem. Eng. Commun.*, Vol. 45, p. 61-73), *Desulfotomaculum kuznetsovii* (DSM 6115), *Desulfotomaculum thermobezoicum* subsp. *thermosyntrophicum* (DSM 14055), *Eubacterium limosum* (DSM 20543), *Methanosarcina acetivorans* C2A (DSM 2834), *Moorella* sp. HUC22-1 (Sakai et al., 2004, *Biotechnol. Let.*, Vol. 29, p. 1607-1612), *Moorella thermoacetica* (DSM 521, formerly *Clostridium thermoaceticum*), *Moorella thermoautotrophica* (DSM 1974), *Oxobacter pfennigii* (DSM 322), *Sporomusa aerivorans* (DSM 13326), *Sporomusa ovata* (DSM 2662), *Sporomusa silvacetica* (DSM 10669), *Sporomusa sphaeroides* (DSM 2875), *Sporomusa termitida* (DSM 4440) and *Thermoanaerobacter kivui* (DSM 2030, formerly *Acetogenium kivui*).

More preferred the strain ATCC BAA-624 of *Clostridium carboxidivorans* is used. Even more preferred the bacterial strain labelled "P7" and "P11" of *Clostridium carboxidivorans* as described for example in U.S. 2007/0275447 and U.S. 2008/0057554 is used.

Another particularly suitable bacterium is *Clostridium ljungdahlii*. In particular, strains selected from the group consisting of *Clostridium ljungdahlii* PETC, *Clostridium ljungdahlii* ERI2, *Clostridium ljungdahlii* COL and *Clostridium ljungdahlii* O-52 may be used in the conversion of synthesis gas to hexanoic acid via the corresponding C2-intermediate. These strains for example are described in WO 98/00558, WO 00/68407, ATCC 49587, ATCC 55988 and ATCC 55989.

Preferably the production of the hexanoic acid is from the ethanol and/or the lower alkanoic acid or any salts thereof which is from synthesis gas and involves the use of the acetogenic bacteria in conjunction with a microorganism capable of carbon chain elongation. For example, *Clostridium ljungdahlii* may be used simultaneously with *Clostridium kluyveri*. In another example, a single acetogenic cell may be capable of the activity of both organisms. For example, the acetogenic bacteria may be *C. carboxidivorans* which may be capable of carrying out both the Wood-Ljungdahl pathway and the carbon chain elongation pathway.

Preferably the lower alkanoic acid or any salts thereof provided in step (a) of the method according to the instant invention is selected from the group consisting of acetic acid and butanoic acid.

Preferably the ethanol and/or the lower alkanoic acid or any salts thereof provided in step (a) of the method according to the instant invention is ethanol in combination with at least one other carbon source selected from the group consisting of acetate, propanoate, butanoate (butyrate) and pentanoate. More preferred, the ethanol and/or the lower alkanoic acid or any salts thereof provided in step (a) of the method according to the instant invention is ethanol and acetate. Alternatively preferred, the ethanol and/or the lower alkanoic acid or any salts thereof provided in step (a) of the method according to the instant invention is a combination of ethanol and butyric acid. But it is also possible to advantageously use as the ethanol and/or the lower alkanoic acid or any salts thereof provided in step (a) of the method according to the instant invention either ethanol or acetate alone.

The microorganism in step (a) of the method according to the instant invention capable of carrying out carbon chain elongation to produce the hexanoic acid and/or the salt thereof and/or the ester thereof, may be any organism that may be capable of carbon-chain elongation as described in Jeon et al. Biotechnol Biofuels (2016) 9:129. The microorganism present in step (a) of the present invention may also include microorganisms which in their wild-type form are not capable of carbon chain elongation, but have acquired this trait as a result of genetic modification. Preferably the microorganism in (a) is selected from the group consisting of *Clostridium carboxidivorans* and *Clostridium kluyveri*, with *Clostridium kluyveri* being most preferred.

The microorganism in step (a) of the method according to the instant invention capable of carrying out carbon chain elongation to produce the hexanoic acid and/or the salt thereof and/or the ester thereof may be cultivated with any culture media, substrates, conditions, and processes generally known in the art for culturing bacteria. This allows for the hexanoic acid and/or the salt thereof and/or the ester thereof to be produced using a biotechnological method. Depending on the microorganism that is used for the production of the hexanoic acid and/or the salt thereof and/or the ester thereof appropriate growth medium, pH, temperature, agitation rate, inoculum level, and/or aerobic, microaerobic, or anaerobic conditions are varied. A skilled person would understand the other conditions necessary to carry out step (a) of the method according to the instant invention. In particular, the conditions during step (a) of the method according to the instant invention in the container (e.g. fermenter) may be varied depending on the microorganisms used. The varying of the conditions to be suitable for the optimal functioning of the microorganisms is within the knowledge of a skilled person.

Step (a) of the method according to the instant invention is preferably carried out in an aqueous medium with a pH between 5 and 8, more preferably between 5.5 and 8 and most preferably between 5.5 and 7. The pressure in step (a) of the method according to the instant invention is preferably between 1 and 10 bar. The microorganisms may be contacted in step (a) of the method according to the instant invention at a temperature ranging from 20° C. to 80° C. Preferably the microorganism is contacted at a temperature ranging from 35° C. to about 42° C.

Preferably for the growth of the microorganism and for its production of the hexanoic acid and/or the salt thereof and/or the ester thereof, the aqueous medium comprises any nutrients, ingredients, and/or supplements suitable for growing the microorganism or for promoting the production of the hexanoic acid and/or the salt thereof and/or the ester thereof. In particular, the aqueous medium may comprise at least one of the following: carbon sources, nitrogen sources, such as an ammonium salt, yeast extract, or peptone; minerals; salts; cofactors; buffering agents; vitamins; and any other components and/or extracts that may promote the growth of the bacteria. The culture medium to be used must be suitable for the requirements of the particular strains. Descriptions of culture media for various microorganisms are given, for example, in "Manual of Methods for General Bacteriology", for example LB medium in the case of *E. coli*, ATCC1754-Medium may be used in the case of *C. ljungdahrn*.

The microorganisms during step (a) of the method according to the instant invention are incubated with the carbon source sufficiently long enough to produce the desired product. For example, for at least 1, 2, 4, 5, 10 or 20 hours.

It may be advantageous, if between step (a) and (b) of the method according to the instant invention the hexanoic acid and/or the salt thereof and/or the ester thereof is purified. This purification step preferably comprises extracting the hexanoic acid and/or the salt thereof and/or the ester thereof from (a) using at least one extractant, preferably selected from alkyl-phosphine oxides and trialkylamines, more preferably the extractant comprises at least one alkyl-phosphine oxide and optionally at least one alkane comprising at least 12 carbon atoms, or at least one trialkylamine and at least one alkane comprising at least 12 carbon atoms; At the end of the purification step comprising extracting, the excess water from the aqueous medium may be removed thus resulting in the extractant containing the extracted hexanoic acid and/or the salt thereof and/or the ester thereof. In particular, at the end of the purification step comprising extracting, with the hexanoic acid and/or the salt thereof and/or the ester thereof extracted and removed, what remains may be the fermentation medium with the cells used for producing the hexanoic acid and/or the salt thereof and/or the ester thereof, and these cells together with the fermentation medium may then be recycled for step (a).

Step (b) of the method according to the instant invention involves (b) contacting the hexanoic acid and/or the salt thereof and/or the ester thereof from (a) with at least one ketonization catalyst under suitable reaction conditions for chemical ketonization of the hexanoic acid and/or the salt thereof and/or the ester thereof to 6-undecanone.

In step (b) of the method according to the instant invention any metal oxide catalyst or mixtures thereof can be used. Ketonization reacts the hexanoic acid and/or the salt thereof and/or the ester thereof to one 6-undecanone with the removal of one water and one carbon dioxide. The mechanism that may be involved in ketonization of hexanoic acid where hexanoic anhydride ($(CH_3(CH_2)_4)COOCO(CH_2)_4CH_3$) may be formed is disclosed at least in Woo, Y., *Ind. Eng. Chem. Res.* 2017, 56: 872-880. Ketonization of hexanoic acid in the presence of a variety of metal oxide catalysts is at also shown in Wang, S. *J. Phys. Chem. C* 2017, 121, 18030-18046.

The ketonization catalyst used in step (b) of the method according to the instant invention preferably is a heterogeneous catalyst for the efficient production of 6-undecanone from biologically produced hexanoic acid according to step (a). In particular, a ketonization catalyst is preferably any metal oxide catalyst or mixtures thereof selected from the group consisting of metal oxide catalyst or mixtures thereof is selected from the group consisting of heteropoly acid ($H_3PW_{12}O_{40}$) catalysts, niobium oxide ($Nb_2O_5$) catalysts, titanium oxide ($TiO_2$) catalysts, cerium oxide ($CeO_2$) catalysts, zinc-chromium (Zn—Cr) mixed oxide catalysts, manganese oxide ($MnO_x$) catalysts, lanthanum oxide ($La_2O_3$) catalysts, magnesium oxide (MgO) catalysts, iron oxide (FeO, $FeO_2$, $Fe_2O_3$, $Fe_3O_4$, $Fe_4O_5$, $Fe_5O_6$, $Fe_5O_7$), silicon-aluminium ($Si_yAl_zO$) mixed oxide catalysts, aluminium oxide ($Al_2O_3$) catalysts and zirconia ($ZrO_2$) catalysts. The 'x' in $MnO_x$ may be 1, 2 or 4. The 'y' and 'z' in $Si_yAl_zO$ may refer to any number where the ratio z/y is any number between 0 to 1.

Exemplary ketonization is carried as disclosed in Pham T. N., *ACS Catal.* 2013, 3: 2456-2473 using a suitable heterogenous hydrogenation metal catalyst and suitable reaction conditions. The conditions as disclosed can vary depending on the catalyst used for effective yield of 6-undecanone.

In yet another example, $MnO_2$ and/or $Al_2O_3$ catalyst may be used based on what is disclosed in Gliński, M. et al, *Polish J. Chem.* 2004, 78: 299-302 for ketonizing hexanoic acid to 6-undecanone.

In a further example, $Nb_2O_5$ catalyst may be used as disclosed in U.S. Pat. No. 6,265,618 B1 especially in example 3 in ketonizing hexanoic acid to 6-undecanone. A skilled person would by simple trial and error be able to identify the suitable catalyst and the appropriate conditions for producing 6-undecanone from hexanoic acid based on the state of the art. Orozco, L. M et al *ChemSusChem,* 2016, 9(17): 2430-2442 and Orozco, L. M et al *Green Chemistry,* 2017, 19(6): 1555-1569 also disclose other catalyst that may be used as ketonization catalysts in step (b) of the method according to the instant invention.

The metal oxide catalyst or mixtures thereof is preferably selected from the group consisting of heteropoly acid ($H_3PW_{12}O_{40}$ catalyst, titanium oxide ($TiO_2$) catalyst, cerium oxide ($CeO_2$) catalyst, zinc-chromium (Zn—Cr) mixed oxide catalyst, manganese oxide ($MnO_2$) catalyst, lanthanum oxide ($La_2O_3$) catalyst, magnesium oxide (MgO) catalyst, iron oxide ($FeO$, $FeO_2$, $Fe_2O_3$, $Fe_3O_4$, $Fe_4O_5$, $Fe_5O_6$, $Fe_5O_7$), silicon-aluminium (Si—Al) mixed oxide catalyst and zirconia ($ZrO_2$) catalyst.

Preferably, the ketonization catalyst in step (b) is a zirconia aerogel catalyst. It can be used in the ketonization of the hexanoic acid and/or the salt thereof and/or the ester thereof as disclosed in Woo, Y., *Ind. Eng. Chem. Res.* 2017, 56: 872-880. Lee, Y. et al in *Applied Catalysis A: General.* 2015, 506: 288-293 discloses different ketonization catalysts and their effectiveness in ketonization the hexanoic acid and/or the salt thereof and/or the ester thereof. A skilled person can very easily use the method described in Lee Y., et al to determine the suitable ketonization catalysts and/or conditions for use in the ketonization of the hexanoic acid and/or the salt thereof and/or the ester thereof.

In particular, suitable reaction conditions of step (b) comprises reaction temperatures of 100° C.-500° C., 100° C.-450° C., 100° C.-400° C., 100° C.-350° C., 100° C.-300° C., 100° C.-250° C., 100° C.-200° C., 150° C.-500° C., 150° C.-450° C., 150° C.-400° C., 150° C.-350° C., 150° C.-300° C., 150° C.-250° C., 150° C.-200° C., 200° C.-500° C., 200° C.-450° C., 200° C.-400° C., 200° C.-350° C., 200° C.-300° C., 200° C.-250° C., 250° C.-500° C., 250° C.-450° C., 250° C.-400° C., 250° C.-350° C., 250° C.-300° C. and the like.

Preferably, the (b) of the method according to the instant invention is carried out at a temperature between 150° C. and 350° C.

Preferably 6 $MgO/SiO_2$ catalyst is the ketonization catalyst in step (b) of the method according to the instant invention and step (b) is carried out at a temperature between 150° C. and 350° C., preferably between 200° C. and 350° C.

Step (c) of the method according to the instant invention provides contacting the 6-undecanone obtained in step (b) with at least one hydrogenation metal catalyst for catalytic hydrogenation of the 6-undecanone to 6-undecanol.

6-undecanol ($C_{11}H_{24}O$), a secondary alcohol, is a result of the catalytic hydrogenation of the 6-undecanone, a molecule of hydrogen is added across the carbon-oxygen double bond to ultimately furnish the 6-undecanol as the final product.

The hydrogenation metal catalyst in the method according to the instant invention may be a homogeneous or heterogeneous catalyst. Homogeneous metal catalysts may be metal complexes that are known in the art.

Preferably the hydrogenation metal catalyst in step (c) in the method according to the instant invention is a heterogeneous catalyst. Some advantages of using multiphase catalytic reactions using solid catalysts include easy separation of catalysts and products, easy recovery, and catalyst recycling, and relatively mild operating conditions. There are also clear economic and environmental incentives in using heterogeneous catalysts.

Preferably the hydrogenation metal catalyst in step (c) in the method according to the instant invention is selected from the group consisting of ruthenium (Ru) catalysts, rhenium (Re) catalysts, nickel (Ni) catalysts, iron (Fe) catalysts, cobalt (Co) catalysts, palladium (Pd) catalysts and platinum (Pt) catalysts.

The hydrogenation metal catalyst of step (c) in the method according to the instant invention is preferably selected from the group consisting of ruthenium (Ru) catalysts, rhenium (Re) catalysts, nickel (Ni) catalysts, iron (Fe) catalysts, cobalt (Co) catalysts and platinum (Pt) catalysts. More preferably the hydrogenation metal catalyst in step (c) in the method according to the instant invention is selected from the group consisting of Ni catalysts, Pd catalysts and Pt catalyst. In one example, the hydrogenation metal catalyst used in step (c) in the method according to the instant invention are nickel nanoparticles as described in Alonso, F. *Tetrahedron,* 2008, 64: 1847-52. In another example, Iron (II) PNP Pincer Complexes may be used as the hydrogenation metal catalyst in step (c) in the method according to the instant invention as disclosed in Gorgas, N., *Organometallics,* 2014, 33 (23): 6905-6914. In yet another example, magnetite nanoparticles of ruthenium (Ru) catalyst, rhenium (Re) catalyst, nickel (Ni) catalyst, iron (Fe), cobalt (Co), palladium (Pd) catalyst or platinum (Pt) catalyst as described in Tariq Shah M., et al., ACS Applied Materials & Interfaces, 2015: 7(12), 6480-9 may be used as the heterogenous hydrogenation metal catalyst in step (c) in the method according to the instant invention.

In yet another example, a copper-phosphine complex is used as a homogeneous hydrogenation metal catalyst in step (c) in the method according to the instant invention as disclosed in Chen, J-X., *Tetrahedron,* 2000, 56: 2153-2166. In a further example, a heterogenous Pt catalyst, in particular a $Pt/Al_2O_3$ catalyst, as disclosed in *Journal of Molecular Catalysis A: Chemical,* 2014, 388-389: 116-122 may be used in step (c) in the method according to the instant invention canol. *ChemSusChem,* 2017: 10(11), 2527-2533 also discloses a variety of heterogenous catalysts such as Pt/C, Ru/C, and Pd/C that may be used in combination with or without an acid catalyst for the hydrogenation of 6-undecanone to 6-undecanol. Based on the above, a skilled person may determine a suitable hydrogenation catalyst to be used in step (c) in the method according to the instant invention to yield 6-undecanol 6-undecanone.

A skilled person would easily be able to determine the suitable hydrogenation metal catalyst and vary the conditions accordingly to efficiently produce 6-undecanol from hydrogenation of 6-undecanone.

In step (d) in the method according to the instant invention esterification of the 6-undecanol with at least one acyl group donor is carried out.

Any kind of acyl group donor can be used for group A) as well as for group B) acyl group donors; these can be for example, the carboxylic acids themselves, their anhydrides or carboxylic acid esters, such as methyl, ethyl ester and/or glycerol esters.

In general, in step (d) in the method according to the instant invention acyl group donors used for group A) as well as for group B) are preferred, which donate acyl groups being preferably contained in the 6-undecanol-esters contained in the compositions according to the instant invention.

Preferably in accordance with the instant invention, the acyl group donor for group A) is selected from triglycerides, especially natural fats and oils, more preferably selected from the group comprising, preferably consisting of, coconut fat, palm kernel oil, olive oil, palm oil, argan oil, castor oil, linseed oil, babassu oil, rapeseed oil, algal oils, sesame oil, soya oil, avocado oil, jojoba oil, safflower oil, almond oil, cottonseed oil, shea butter, sunflower oil, cupuacu butter and oils having a high proportion of polyunsaturated fatty acids (PUFAS). It is likewise possible with preference to use sorbitan esters, monoglycerides and diglycerides having above-described chain length distributions and modifications.

In step (d) in the method according to the instant invention the esterification can be carried out by classical esterification methods. The esterification can be carried out non-catalyzed, catalyzed with enzymes, acid- or base-catalyzed.

In step (d) in the method according to the instant invention the esterification can be an esterification by enzyme catalysis, which is a preferred esterification kind.

This can be carried out for example with at least one lipase.

Preferably, the lipase used in the esterification by enzyme catalysis in step (d) in the method according to the instant invention is one that can be isolated from an organism from the realm of fungi, and those lipases having at least 60%, preferably at least 80%, more preferably at least 90%, especially preferably at least 95%, 98% or 99%, homology at the amino acid level to those that can be isolated from an organism from the realm of fungi.

The enzymes that are homologous at the amino acid level, by comparison with the reference sequence, preferably have at least 50%, especially at least 90%, enzyme activity in propyl laurate units. The measured activity of the carboxylic ester hydrolase in propyl laurate units is measured at the temperature optimal for the given enzyme, where "optimal temperature" is understood to mean that temperature at which the enzyme has its highest activity. For lipases A and B with accession number P41365 from *Candida antarctica*, for example, the optimal temperature is 60° C.

"Homology at the amino acid level" in the context of the present invention shall be understood here and hereinafter to mean "amino acid identity", which can be determined with the aid of known methods. In general, use is made of special computer programs with algorithms taking into account specific requirements. Preferred methods for determining the identity initially generate the greatest alignment between the sequences to be compared. Computer programs for determining the identity include, but are not limited to, the GCG program package including GAP (Deveroy, J. et al., Nucleic Acid Research 12 (1984), page 387, Genetics Computer Group University of Wisconsin, Medicine (WI), and BLASTP, BLASTN and FASTA (Altschul, S. et al., Journal of Molecular Biology 215 (1990), pages 403-410. The BLAST program can be obtained from the National Center For Biotechnology Information (NCBI) and from other sources (BLAST Handbook, Altschul S. et al., NCBI NLM NIH Bethesda ND 22894; Altschul S. et al., above).

The person skilled in the art is aware that various computer programs are available for the calculation of similarity or identity between two nucleotide or amino acid sequences. For instance, the percentage identity between two amino acid sequences can be determined, for example, by the algorithm developed by Needleman and Wunsch (J. Mol. Biol. (48): 444-453 (1970)), which has been integrated into the GAP program in the GCG software package (available at http://www.gcg.com), using either a Blossom 62 matrix or a PAM250 matrix, a gap weight of 16, 14, 12, 10, 8, 6 or 4 and a length weight of 1, 2, 3, 4, 5 or 6. The person skilled in the art will recognize that the use of different parameters will lead to slightly different results, but that the percentage identity between two amino acid sequences overall will not be significantly different. Typically, the Blossom 62 matrix is utilized with employment of the default settings (gap weight: 12, length weight: 1).

In the context of the present invention, an identity of 60% according to the above algorithm means 60% homology. The same applies to higher identities.

Lipases used with particular preference in the esterification by enzyme catalysis in step (d) in the method according to the instant invention are enzymes selected from the group of the lipase from *Thermomyces lanuginosus* with accession number 059952, lipases A and B with accession number P41365 from *Candida antarctica* and the lipase from *Mucor miehei* with accession number P19515, the lipase from *Humicola* sp. with accession number O59952, the lipase from *Rhizomucor javanicus* with accession number S32492, the lipase from *Rhizopus oryzae* with accession number P61872, the lipases from *Candida rugosa* with accession number P20261, P32946, P32947, P3294 and P32949, the lipase from *Rhizopus niveus* with accession number P61871, the lipase from *Penicillium camemberti* with accession number P25234, the lipases from *Aspergillus niger* with accession number ABG73613, ABG73614 and ABG37906 and the lipase from *Penicillium cyclopium* with accession number P61869, and their respective at least 60%, preferably at least 80%, more preferably at least 90%, especially preferably at least 95%, 98% or 99%, homologues at the amino acid level. With regard to homology, reference is made to the definition given above.

Commercial examples, and carboxylic ester hydrolyses that are likewise used with in the esterification by enzyme catalysis in step (d) in the method according to the instant invention are the commercial products Lipozyme TL IM, Novozym 435, Lipozyme IM 20, Lipase SP382, Lipase SP525, Lipase SP523, (all commercial products from Novozymes A/S, Bagsvaerd, Denmark), Chirazyme L2, Chirazyme L5, Chirazyme L8, Chirazyme L9 (all commercial products from Roche Molecular Biochemicals, Mannheim, Germany), CALB Immo Plus TM from Purolite, and Lipase M "Amano", Lipase F-AP 15 "Amano", Lipase AY "Amano", Lipase N "Amano", Lipase R "Amano", Lipase A "Amano", Lipase D "Amano", Lipase G "Amano" (all commercial products from Amano, Japan).

The esterification by enzyme catalysis in step (d) in the method according to the instant invention is preferably conducted at reaction temperatures in the range between 20° C. and 160° C., preferably 25° C. and 130° C., especially between 30° C. and 90° C.

The esterification by enzyme catalysis in step (d) in the method according to the instant invention is preferably conducted at a pressure of less than 1 bar, preferably less than 0.5 bar and more preferably less than 0.05 bar.

In an alternative preferred embodiment, the esterification by enzyme catalysis in step (d) in the method according to the instant invention is conducted at a pressure of greater than 1 bar, preferably within a range from 2 bar to 10 bar. In this connection, it is preferable that the reaction mixture is provided with an inert gas; these are preferably selected from the group comprising, preferably consisting of, nitrogen and argon.

Acid catalyzed esterification in step (d) in the method according to the instant invention can be done, for example, with Brönsted- or Lewis acids. Examples are hydrochloric acid, sulfonic acids (such as methane sulfonic acid, para-toluene sulfonic acid, 10-camphersulfonic acid), sulfuric acid, phosphoric acid, hypophosphorous acid, phosphonic acid, phosphorous acid, phosphinic acid, tin-(II) salts such as tin oxide, zinc salts such as zinc oxide or zinc acetylacetonate or zirconium salts. Also, polymer-/resin-based or supported catalysts can be used, such as sulfonated polystyrene. The above-mentioned acids can also be used in combination.

Base catalysis esterification in step (d) in the method according to the instant invention can for example be carried out with alkaline, earth alkaline or ammonium salts such as the respective hydroxides, oxides, phosphates or carbonates. Furthermore, amines or the alkaline salts of alcohols or of organic acids can be used as bases. Also, the above-mentioned bases can be used in combination.

Temperatures of 30-260° C., preferably at 100-200° C., are typically used in acid or based catalyzed esterifications in step (d) in the method according to the instant invention. A vacuum and/or a flow of an inert gas like nitrogen or argon can also be applied to support the condensation of the water.

The present invention further provides for the use of at least one 6-undecanol-ester selected from 6-undecanol-esters obtainable by esterification of undecan-6-ol with one selected from A) monocarboxylic acids with 6 to 32, preferably 6 to 22, more preferably 8 to 22 carbon atoms, and B) polyfunctional carboxylic acids with 2 to 44, preferably 3 to 38, more preferably 4 to 18, carbon atoms, preferably tricarboxylic and dicarboxylic acids, more preferably dicarboxylic acids with 2 to 18, preferably 3 to 13, more preferably 4 to 11, carbon atoms (identical to those 6-undecanol-ester comprised in the aqueous composition according to the instant invention)

or obtainable by the method according to the invention for preparation of a cosmetic formulation.

The present invention further provides for the use of at least one 6-undecanol-ester comprised in the aqueous composition according to the instant invention or obtainable by the method according to the invention for avoidance of skin dryness.

The present invention further provides for the use of at least one 6-undecanol-ester comprised in the aqueous composition according to the instant invention or obtainable by the method according to the invention for solubilization of active ingredients and UV light protection filters, preferably UV light protection filters, more preferably organic UV light protection filters, in cosmetic formulations.

The present invention further provides for the use of at least one 6-undecanol-ester comprised in the aqueous composition according to the instant invention or obtainable by the method according to the invention for providing a good, non-tacky skin feel of the cosmetic formulation.

The present invention further provides for the use of at least one 6-undecanol-ester comprised in the aqueous composition according to the instant invention or obtainable by the method according to the invention for a reduced ability of a cosmetic formulation to distribute on skin or hair. This is beneficial for the use in eye or face care formulations.

The present invention further provides for the use of at least one 6-undecanol-ester comprised in the aqueous composition according to the instant invention or obtainable by the method according to the invention for stabilizing cosmetic formulations in the form of emulsions, preferably at pH values below pH 5 and/or temperatures below 15° C.

The use according to the invention is a cosmetic use.

The examples adduced hereinafter describe the present invention by way of example, without any intention that the invention, the scope of application of which is apparent from the entirety of the description, be restricted to the embodiments specified in the examples.

The following FIGURES are part of the examples:

The FIGURE shows emulsions after repeated freezing/thawing.

EXAMPLES

Example 1: Synthesis of 6-dodecanol from Ethanol and Acetate

Cultivation of *Clostridium kluyveri* and Extraction of Hexanoic Acid

The bacterium *Clostridium kluyveri* was cultivated for the biotransformation of ethanol and acetate to hexanoic acid. For the inSitu extraction of the produced hexanoic acid a mixture of tetradecane with trioctylphosphineoxide (TOPO) was continuously passed through the cultivation. All cultivation steps were carried out under anaerobic conditions in pressure-resistant glass bottles that can be closed airtight with a butyl rubber stopper.

The precultivation of *Clostridium kluyveri* was carried out in a 1000 mL pressure-resistant glass bottle in 250 ml of EvoDM45 medium (pH 5.5; 0.004 g/L Mg-acetate, 0.164 g/l Na-acetate, 0.016 g/L Ca-acetate, 0.25 g/l K-acetate, 0.107 mL/L $H_3$Pat (8.5%), 2.92 g/l Na-acetate, 0.35 mg/L Co-acetate, 1.245 mg/L Ni-acetate, 20 pg/L d-biotin, 20 µg/L folic acid,10 µg/L pyridoxine-HCl, 50 µg/L thiamine-HC, 50 pg/L Riboflavin, 50 pg/L nicotinic acid, 50 µg/L Ca-pantothenate, 50 µg/L Vitamin B12, 50 µg/L p-aminobenzoate, 50 µg/L lipoic acid, 0.702 mg/L $(NH_4)_2Fe(SO_4)_2 \times 4\ H_2O$, 1 ml/L KS-acetate (93,5 mM), 20 mL/L ethanol, 0.37 g/L acetic acid) at 37° C., 150 rpm and a ventilation rate of 1 L/h with a mixture of 25% $CO_2$ and 75% $N_2$ in an open water bath shaker. The gas was discharged into the headspace of the reactor. The pH was hold at 5.5 by automatic addition of 2.5 M $NH_3$ solution. Fresh medium was continuously fed to the reactor with a dilution rate of 2.0 $d^{-1}$ and fermentation broth continuously removed from the reactor through a KrosFlo® hollow fiber polyethersulfone membrane with a pore size of 0.2 µm (Spectrumlabs, Rancho Dominguez, USA) to retain the cells in the reactor and hold an $OD_{600nm}$ of ~1.5.

For the main culture 150 ml of EvoDM39 medium (pH 5.8; 0.429 g/L Mg-acetate, 0.164 g/l Na-acetate, 0.016 g/L Ca-acetate, 2.454 g/l K-acetate, 0.107 mL/L $H_3PO_4$ (8.5%), 1.01 mL/L acetic acid, 0.35 mg/L Co-acetate, 1.245 mg/L Ni-acetate, 20 µg/L d-biotin, 20 µg/L folic acid, 10 µg/L pyridoxine-HCl, 50 µg/L thiamine-HCl, 50 µg/L Riboflavin, 50 µg/L nicotinic acid, 50 µg/L Ca-pantothenate, 50 µg/L Vitamin B12, 50 µg/L p-aminobenzoate, 50 µg/L lipoic acid, 0.702 mg/L $(NH_4)_2Fe(SO_4)_2 \times 4\ H_2O$, 1 ml/L KS-acetate (93,5 mM), 20 mL/L ethanol, 8.8 mL $NH_3$ solution (2,5 mol/L), 27.75 ml/L acetic acid (144 g/L)) were inoculated in a 1000 ml bottle with 100 ml cell broth from the preculture to an $OD_{600nm}$ of 0.71.

The cultivation was carried out at 37° C., 150 rpm and a ventilation rate of 1 L/h with a mixture of 25% $CO_2$ and 75% $N_2$ in an open water bath shaker for 65 h. The gas was discharged into the headspace of the reactor. The pH was held at 5.8 by automatic addition of 2.5 M $NH_3$ solution. Fresh medium was continuously fed to the reactor with a dilution rate of 0.5 $d^{-1}$ and fermentation broth continuously removed from the reactor by holding an $OD_{600nm}$ of ~0.5. Additional 120 g of a mixture of 6% (w/w) TOPO in tetradecane was added to the fermentation broth. Then this organic mixture was continuously fed to the reactor and the organic phase also continuously removed from the reactor with a dilution rate of 1 $d^{-1}$.

During cultivation several 5 mL samples from both, the aqueous and the organic phase, were taken to determinate $OD_{600nm}$, pH and product formation. The determination of the product concentrations was performed by semiquantitative 1H-NMR spectroscopy. As an internal quantification standard sodium trimethylsilylpropionate (T(M)SP) was used.

During the main cultivation in the aqueous phase a steady state concentration of 8.18 g/L ethanol, 3.20 g/L acetate, 1.81 g/L butyrate and 0.81 g/L hexanoate was reached. The $OD_{600nm}$ remained stable at 0.5. In the organic phase a steady state concentration of 0.43 g/kg ethanol, 0.08 g/kg acetate, 1.13 g/kg butyrate and 8.09 g/kg hexanoate was reached. After the experiment the cells remained viable while transferred to further cultivations.

The distribution coefficient $K_D$ of the substrates and products in the system aqueous medium and 6% TOPO in tetradecane was calculated from the concentrations in both phases.

$$K(D) = \frac{c(\text{organic phase})}{c(\text{aqueous phase})}$$

The $K_D$ in the steady state was 0.05 for ethanol, 0.03 for acetic acid, 0.62 for butyric acid and 9.99 for hexanoic acid.

Ketonization of Hexanoic Acid to 6-undecanone

The ketonization was conducted in a heated continuous flow-bed reactor. At first, the reactor was charged with magnesium oxide on silica (50 wt. %, 14.00 g) and heated under an argon flow (54 mL/min) at 330° C. for one hour. The temperature was raised to 360° C. Than a mixture of hexanoic acid in tetradecane (v/v: 3/1) was continuously fed to the reactor with a rate of 3.3 mL/h. The gaseous out stream was collected by two cooling traps, which were cooled with water and a mixture of dry ice and isopropanol. The collected fractions were weighted and analyzed by gas chromatography (GC) for their composition. In total, 370.65 g of hexanoic acid was fed to the reactor, which equals to a maximum theoretical yield of 271.70 g of 6-undecanone and 28.75 g of water and 70.21 g of carbon dioxide as by-products. The obtained amount of 6-undecanone was 267.67 g and the amount of water was 28.32 g. This corresponds to a 99% mass recovery at full conversion. The high productivity and selectivity were confirmed by regular GC measurements, as only traces of hexanoic acid and no side-products were detected.

Hydrogenation of 6-undecanone to 6-undecanol

The hydrogenation reaction for 6-undecanone to 6-undecanol was performed in a 300 ml autoclave reactor (PARR Instrument Company). The reactor was placed in an aluminum block and the temperature was controlled by a thermocouple placed inside the reactor. Typically, 30 mg of solid catalyst, 170.3 mg, 1.0 mmol of substrate was added to a 4 ml glass vial having an oven dried magnetic stirrer. 2.0 ml of dry Toluene was used as solvent, vial was fitted with a screw cap and a needle was inserted through the septum. The vial was placed in the reactor. The reactor was purged three times with 10 bar of $H_2$ and then the pressure was increased to 20 bar. The reactor was heated to the desired temperature of 120° C. for 20 h. After the reaction, the reactor was cooled down to 5° C. using an ice bath, the gas phase was slowly released, and the remaining liquid was carefully separated from the solid catalyst and was analyzed separately using an internal standard (100 µL n-hexadecane).

The catalyst 3.0 Co@γ-$Al_2O_3$ showed 99% ketone conversion and an alcohol yield of 98%. The catalyst preparation method was as follows:

3 wt % Co@γ-$Al_2O_3$, using Ascorbic acid as reductant and glucose as capping agent in $H_2O$, Pyrolysis at 800° C. for 2 h, Co salt is Cobalt(II) nitrate hexahydrate. In a typical synthesis, 149 mg, 0.51 mmol of $Co(NO_3)_2$. $6H_2O$ was dissolved in 20 ml D.I $H_2O$ followed by the stepwise addition of aqueous solutions of 265 mg, 3.0 mmol ascorbic acid and 92 mg, 1 mmol of D-(+)-glucose. The contents were stirred at 90° C. for 2-3 h. Next, 1.0 g of γ-$Al_2O_3$ support was added and the slurry was stirred overnight at R.T. Excess water was removed through centrifugation and the solids were dried in oven at 120° C. for 10 h and then pyrolyzed at 800° C. for 2 h under argon atmosphere.

Example 2: Undec-6-yl Hexanoate

A mixture of undecan-6-ol (172.3 g/mol, 100.0 g, 0.58 mol) and hexanoic acid (min. 98% (purified ntermediate from Example 1), 116.2 g/mol, 70.9 g, 0.61 mol) was heated under catalytic addition of 0.17 g para-toluene sulfonic acid and stirred at 160° C. The resulting water was continuously distilled off in vacuum and under a flow of nitrogen until an acidity of less than 20 mg KOH/g was reached. The product was neutralized with potassium hydroxide solution and subsequently filtered, washed with water and distilled in vacuum. A colorless to slightly yellow oil was obtained. Saponification value: 207 mg KOH/g. Purity (GC): >98%.

Example 3: Undec-6-yl Laurate

A mixture of undecan-6-ol (172.3 g/mol, 100.0 g, 0.58 mol) and lauric acid (min. 99% (from Sigma-Aldrich), 200.3 g/mol, 116.2 g, 0.58 mol) was heated under catalytic addition of 1.1 g para-toluene sulfonic acid and stirred to 150° C. The resulting water was continuously distilled off in vacuum and under a flow of nitrogen until an acidity of less than 20 mg KOH/g was reached. The product was neutralized with potassium hydroxide solution and subsequently filtered, washed with water and distilled in vacuum. A colorless to slightly yellow oil was obtained.

Saponification value: 158 mg KOH/g. Purity (GC): >98%.

Example 4: Undec-6-yl Stearate

A mixture of undecan-6-ol (172.3 g/mol, 100.0 g, 0.58 mol) and stearic acid (min. 92%, Palmac 90-18 (from IOI), acid value 199 mg KOH/g, 284 g/mol, 156.2 g, 0.55 mol) was heated under catalytic addition of 0.26 g of tin(II)oxide and stirred at 180° C. The resulting water was continuously distilled off in vacuum and under a flow of nitrogen until an acidity of less than 20 mg KOH/g was reached.

The product was neutralized with potassium hydroxide solution and subsequently filtered, bleached with $H_2O_2$ solution and washed with water. After drying a slightly yellowish wax was obtained. Acid value: <1 mg KOH/g; Saponification value: 129 mg KOH/g. Purity (GC): >95%.

Example 5: Undec-6-yl Caprylate/Caprate

A mixture of undecan-6-ol (172.3 g/mol, 100.0 g, 0.58 mol) and caprylic/capric acid (Kortacid 0810 (from Oleon), acid value 360 mg KOH/g, 156 g/mol, 95.2 g, 0.61 mol) was heated under catalytic addition of 0.2 g para-toluene sulfonic acid and stirred at 160° C. The resulting water was continuously distilled off in vacuum and under a flow of nitrogen until an acidity of less than 20 mg KOH/g was reached. The product was neutralized with potassium hydroxide solution and subsequently filtered, washed with water and distilled in vacuum. A slightly yellowish oil was obtained.

Saponification value: 181 mg KOH/g. Purity (GC): >97%.

Example 6: Undec-6-yl Cocoate

A mixture of undecan-6-ol (172.3 g/mol, 100.0 g, 0.58 mol) and distilled coconut fatty acid (Wilfarin DC-0818 (from Wilmar), acid value 270 mg KOH/g, 208 g/mol, 114.4 g, 0.55 mol) was heated under catalytic addition of 0.43 g of tin(II)oxide and stirred at 160° C. The resulting water was continuously distilled off in vacuum and under a flow of nitrogen until an acidity of less than 20 mg KOH/g was reached. The product was neutralized with potassium hydroxide solution and subsequently filtered, bleached with $H_2O_2$ solution and washed with water. After drying a yellowish oil was obtained.

Acid value: 1 mg KOH/g; Saponification value: 156 mg KOH/g. Purity (GC): >95%.

Example 7: Undec-6-yl 12-Hydroxystearate

A mixture of undecan-6-ol (172.3 g/mol, 100.0 g, 0.58 mol) and 12-hydroxystearic acid (H.C.O. Fatty Acid (from Jayant), acid value 182 mg KOH/g, 308 g/mol, 169.4 g, 0.55 mol) was heated under catalytic addition of 0.27 g of tin(II)oxide and stirred at 180° C. The resulting water was continuously distilled off in vacuum and under a flow of nitrogen until an acidity of less than 20 mg KOH/g was reached. The product was neutralized with potassium hydroxide solution and subsequently filtered, bleached with $H_2O_2$ solution and washed with water. After drying a yellowish wax was obtained.

Acid value: 1 mg KOH/g; Saponification value: 122 mg KOH/g. Purity (GC): >92%.

Example 8: Undec-6-yl Isostearate

A mixture of undecan-6-ol (172.3 g/mol, 100.0 g, 0.58 mol) and isostearic acid (PRISORINE 3503 (from Croda), acid value 190 mg KOH/g, 295 g/mol, 162.3 g, 0.55 mol) was heated under catalytic addition of 0.13 g of tin(II)oxide and stirred at 180° C. The resulting water was continuously distilled off in vacuum and under a flow of nitrogen until an acidity of less than 20 mg KOH/g was reached. The product was neutralized with potassium hydroxide solution and subsequently filtered, bleached with $H_2O_2$ solution and washed with water. After drying a yellowish oil was obtained. Acid value: 2 mg KOH/g; Saponification value: 125 mg KOH/g. Purity (GC): >90%.

Example 9: Undec-6-yl Oleate

A mixture of undecan-6-ol (172.3 g/mol, 100.0 g, 0.58 mol) and oleic acid (Wilfarin OA 7075 (from Wilmar), acid value 200 mg KOH/g, 281 g/mol, 154.6 g, 0.55 mol) was heated under catalytic addition of 0.25 g of tin(II)oxide and stirred at 180° C. The resulting water was continuously distilled off in vacuum and under a flow of nitrogen until an acidity of less than 20 mg KOH/g was reached. The product was neutralized with potassium hydroxide solution and subsequently filtered, bleached with $H_2O_2$ solution and washed with water. After drying a yellow oil was obtained.

Acid value: 1 mg KOH/g; Saponification value: 128 mg KOH/g. Purity (GC): >92%.

Example 10: Bis(undec-6-yl)malate

A mixture of undecan-6-ol (172.3 g/mol, 100.0 g, 0.58 mol) and D,L-malic acid (min. 98% (from Sigma-Aldrich), 134.1 g/mol, 37.5 g, 0.28 mol) was heated under catalytic addition of 0.14 g para-toluene sulfonic acid and stirred at 160° C. The resulting water was continuously distilled off in vacuum and under a flow of nitrogen until an acidity below 30 mg KOH/g was reached. The product was neutralized with potassium hydroxide solution and subsequently filtered and washed with water. After drying a yellowish oil was obtained.

Acid value: 2 mg KOH/g; Saponification value: 255 mg KOH/g. Purity (GC): >90%.

Example 11: Bis(undec-6-yl)succinate

A mixture of undecan-6-ol (172.3 g/mol, 100.0 g, 0.58 mol) and succinic acid (min. 99% (from Sigma-Aldrich), 118.9 g/mol, 33.3 g, 0.28 mol) was heated under catalytic addition of 0.13 g para-toluene sulfonic acid and stirred at 180° C. The resulting water was continuously distilled off in vacuum and under a flow of nitrogen until an acidity below 30 mg KOH/g was reached. The product was neutralized with potassium hydroxide solution and subsequently filtered and washed with water. After drying a slightly yellowish wax was obtained.

Acid value: 2 mg KOH/g; Saponification value: 262 mg KOH/g. Purity (GC): >90%.

Example 12: Bis(undec-6-yl)sebacate

A mixture of undecan-6-ol (172.3 g/mol, 100.0 g, 0.58 mol) and sebacic acid (min. 99% (from Sigma-Aldrich), 202.3 g/mol, 56.6 g, 0.28 mol) was heated under catalytic addition of 0.8 g para-toluene sulfonic acid and stirred at 180° C. The resulting water was continuously distilled off in vacuum and under a flow of nitrogen until an acidity below 30 mg KOH/g was reached. The product was neutralized with potassium hydroxide solution and subsequently filtered and washed with water. After drying a yellowish wax was obtained.

Acid value: 1 mg KOH/g; Saponification value: 223 mg KOH/g. Purity (GC): >90%.

Example 13: Furan-2, 5-dicarboxylic acid bis(undec-6-yl)ester

A mixture of undecan-6-ol (172.3 g/mol, 100.0 g, 0.58 mol) and dimethyl furan-2,5-dicarboxylate (min. 99% (from Sigma-Aldrich), 184.1 g/mol, 53.4 g, 0.29 mol) was heated under catalytic addition of 0.15 g para-toluene sulfonic acid and stirred at 150° C. The resulting methanol was continuously distilled off in vacuum until an acidity of approx. 20 mg KOH/g was reached. The product was neutralized with potassium hydroxide solution and subsequently filtered and washed with water. After drying a yellowish oil was obtained.

Acid value: 2 mg KOH/g; Saponification value: 260 mg KOH/g. Purity (GC): >85%.

Example 14: Tris(undec-6-yl)citrate

A mixture of undecan-6-ol (172.3 g/mol, 100.0 g, 0.58 mol) and citric acid (min. 99% (from Sigma-Aldrich), 192.1 g/mol, 34.6 g, 0.18 mol) was heated under catalytic addition of 0.13 g para-toluene sulfonic acid and stirred at 180° C. The resulting water was continuously distilled off in vacuum and under a flow of nitrogen until an acidity of approx. 30 mg KOH/g was reached. The product was neutralized with potassium hydroxide solution and subsequently filtered and washed with water. After drying a yellowish wax was obtained.

Acid value: 2 mg KOH/g; Saponification value: 260 mg KOH/g. Purity (GC): >85%.

Example 15: Application Testings

In order to show the advantageous property of aqueous compositions comprising 6-undecanol-esters, the following W/O emulsions have been prepared using common methods. The water phase was added slowly and incorporated into the oil phase. The mixture was subsequently homogenized. As reference substrate TEGOSOFT DC (Decyl Cocoate) was used in the comparative example which is not in the scope of this invention.

To evaluate the freeze stability the following formulations for a body lotion were subjected to two freeze thaw cycles from room temperature to −15° C. and back to room temperature. The freeze stability of the aqueous compositions was determined by visual inspection after the samples reached room temperature again. The following terminology was used to describe the freeze stability:

| Freeze stability | |
| --- | --- |
| Very good (++) | No or minimal water separation |
| Good (+) | Very weak water separation |
| Medium (0) | Weak water separation |
| Weak (−) | Strong water separation |
| Very weak (−−) | Very strong oil separation |

The sensory of the cosmetic emulsions are evaluated by a trained sensory panel. At least 5 persons are evaluating the sensory profile of the formulations without knowing the composition of the evaluated samples. The properties the majority of the panellists have described is reported in the table below; given numbers are weight percentages.

Body Lotion

| Phase | Ingredient | A | B* | C* |
| --- | --- | --- | --- | --- |
| A | ISOLAN ® GPS | 2.5 | 2.5 | 2.5 |
| | TEGOSOFT ® DC (Decyl Cocoate) | 21.0 | — | — |
| | Example 3 | — | 21.0 | — |
| | Example 11 | | | 21.0 |
| | Bees wax | 0.2 | 0.2 | 0.2 |
| | Castor wax | 0.3 | 0.3 | 0.3 |
| | Dermofeel ® Toco 70 non GMO | 0.2 | 0.2 | 0.2 |
| B | Verstatil PC (Phenoxyethanol; Carpylyl Glycol) | 0.8 | 0.8 | 0.8 |
| C | Glycerin | 3.0 | 3.0 | 3.0 |
| | Water | 70.5 | 70.5 | 70.5 |
| | Zink sulphate*7 H$_2$O | 1.5 | 1.5 | 1.5 |
| | Freeze stability | (−) | (++) | (++) |
| | Sensory characterization | During distribution: easy to distribute, light, non-tacky 5 minutes after absorption: non-tacky, medium level of residue, not slippery | During distribution: typical distribution behaviour, very light, non-waxy 5 minutes after absorption: high absorption, smooth, slippery | During distribution: typical distribution behaviour, very light, non-tacky 5 minutes after absorption: high absorption, light, slippery |

*According to the invention

In FIG. 1 formulation B containing example 3 is shown on the left in comparison to formulation A containing Decyl Cocoate on the right after freeze-thaw-cycles.

The sensory results surprisingly show lower distribution ability for the systems containing the inventive examples compared to the reference sample while showing high absorption as well as slippery properties 5 minutes after absorption. After the freeze stability test the inventive systems show no signs of instability whereas the comparative sample shows strong water separation which is not acceptable for cosmetic formulations.

Example 16: Further Exemplary Aqueous Compositions Comprising 6-undecanol-esters According to the Invention The following examples demonstrate the versatile applicability of 6-undecanol-esters in different cosmetic formulations and their compatibility with various other ingredients such as emulsifiers, stabilizers, preservatives or active compounds like UV-filters or antimicrobial drugs which are usually challenging to formulate. The application of the invention is not limited to the formulations shown. The preparation of the examples has been done according to common standard methods.

Natural Body Spray

| Phase | Ingredient | w/w-% | w/w-% | w/w-% | w/w-% |
|---|---|---|---|---|---|
| A | TEGO ® Care LTP (Sorbitan Laurate; Polyglyceryl-4 Laurate; Dilauryl Citrate) | 2.50 | 3.00 | | |
| | TEGO ® Care PBS 6 (Polyglyceryl-6 Stearate; Polyglyceryl-6 Behenate) | | | 3.00 | 3.00 |
| | Example 2 | 12.50 | | 12.00 | |
| | Example 10 | | 14.00 | | 9.50 |
| B | Water | Ad 100 | Ad 100 | Ad 100 | Ad 100 |
| | Glycerin | 3.00 | 3.00 | 3.00 | 4.00 |
| | Gellan Gum (Kelcogel CG-HA, CP Kelco) | 0.10 | 0.10 | 0.10 | 0.15 |
| C | dermsosoft ® OMP (Methylpropandiol; Caprylyl Glycol; Penylpropanol) | 2.50 | 2.50 | 2.50 | 2.50 |

W/O Cream

| Phase | Ingredient | w/w-% | w/w-% | w/w-% |
|---|---|---|---|---|
| A | ISOLAN ® PDI (Diisostearoyl Polyglyceryl-3 Dimer Dilinoleate) | 3.00 | | |
| | ISOLAN ® 17 (Polyglyceryl-4 Diisostearate/Polyhydroxystearate/Sebacate (and) Caprylic/Capric Triglyceride (and) Polyglyceryl-3 Oleate (and) Diisostearoyl Polyglyceryl-3 Dimer Dilinoleate) | | 3.00 | 3.00 |
| | Hydrogenated Castor Oil | 0.40 | 0.40 | 0.40 |
| | Beeswax | 0.60 | 0.60 | 0.60 |
| | TEGOSOFT ® CT (Caprylic/Capric Triglyceride) | 5.00 | 5.00 | 5.00 |
| | TEGOSOFT ® P (Isopropyl Palmitate) | 5.00 | 5.00 | 5.00 |
| | TEGOSOFT ® OER (Oleyl Erucate) | 3.00 | 3.00 | 3.00 |
| | Prunus Amygdalus Dulcis (Sweet Almond) Oil | 3.00 | 3.00 | 3.00 |
| | Example 3 | 6.00 | 7.00 | 3.00 |
| | Example 11 | | | 4.00 |
| B | Water | ad 100 | ad 100 | ad 100 |
| | Glycerin | 5.00 | 5.00 | 3.00 |
| C | Magnesium Sulfate Heptahydrate | 1.00 | 1.50 | 0.90 |
| | Sodium Benzoate, Potassium Sorbate, Water (Euxyl K 712, Schülke & Mayr) | 0.50 | 0.50 | 0.50 |
| | Citric Acid (10% in water) | q.s. | q.s. | q.s. |

Anti-Aging Day Cream

| Phase | Ingredient | w/w-% | w/w-% | w/w-% |
|---|---|---|---|---|
| A | ABIL ® EM 90 (Cetyl PEG/PPG-10/1 Dimethicone Triglyceride) | 3.00 | | |
| | ABIL ® EM 180 (Cetyl PEG/PPG-10/1 Dimethicone Triglyceride) | | 2.00 | |
| | ABIL ® WE 09 (Polyglyceryl-4 Isostearate; Cetyl PEG/PPG-10/1 Dimethicone; Hexyl Laurate) | | | 4.00 |
| | TEGOSOFT ® AC (Isoamyl Cocoate) | 5.00 | 4.00 | 5.00 |
| | TEGOSOFT ® DEC (Diethylhexyl Carbonate) | 6.00 | 5.00 | 5.00 |
| | Example 4 | 7.00 | | 6.00 |
| | Example 12 | | 10.00 | 2.00 |
| | HyaCare ® Filler CL (Aqua, Ethylhexyl Stearate, Sodium Hyaluronate Crosspolymer, Polyglyceryl-4 Diisostearate/Polyhydroxystearate/Sebacate, Sodium Isostearate) | 2.50 | 2.50 | 2.50 |
| | Tocopherol | 0.50 | 0.50 | 0.50 |
| | Methyl Methacrylate Crosspolymer (Covabead LH 85, Sensient) | 2.00 | 2.00 | 2.00 |
| B | Water | ad 100 | ad 100 | ad 100 |
| | Sodium Chloride | 0.80 | 0.80 | 0.80 |
| | Glycerin | 4.00 | 4.00 | 4.00 |
| | Butylene Glycol | 4.00 | 4.00 | 4.00 |

-continued

| Phase | Ingredient | w/w-% | w/w-% | w/w-% |
|---|---|---|---|---|
| | TEGO ® Pep 4-Even (Tetrapeptide-30; Glycerin) | 2.50 | 2.50 | 2.50 |
| | Sodium Ascorbyl Palmitate | 1.50 | 1.50 | 1.50 |
| | Urea | 2.50 | 2.50 | 2.50 |
| | Sodium Bisulfite | 0.10 | 0.10 | 0.10 |
| Z | Preservative, Perfume | q.s. | q.s. | q.s. |

Light & Caring Cream

| Phase | Ingredient | w/w-% | w/w-% |
|---|---|---|---|
| A | ABIL ® EM 90 (Cetyl PEG/PPG-10/1 Dimethicone) | 2.00 | 1.50 |
| | ABIL ® EM 97 S (Bis-PEG/PPG-14/14 Dimethicone (and) Dimethicone) | | 1.00 |
| | TEGOSOFT ® OP (Ethylhexyl Palmitate) | 5.00 | 5.00 |
| | TEGOSOFT ® CT (Caprylic/Capric Triglyceride) | 5.00 | 5.00 |
| | TEGOSOFT ® DEC (Diethylhexyl Carbonate) | 10.00 | 10.00 |
| | Example 5 | 6.00 | 6.00 |
| | dermofeel ® viscolid (Hydrogenated Vegetable Oil) | 0.50 | 0.50 |
| B | Water | ad 100 | ad 100 |
| | Sodium Chloride | 0.50 | 0.50 |
| C | Phenoxyethanol, Ethylhexylglycerin (euxyl ® PE 9010, Schülke & Mayr) | 0.80 | 0.80 |

Serum

| Phase | Ingredient | w/w-% |
|---|---|---|
| A | TEGO ® Care 165 (Glyceryl Stearate; PEG-100 Stearate) | 3.00 |
| | TEGO ® Alkanol 18 (Stearyl Alcohol) | 0.50 |
| | Isononyl Isononanoate | 4.00 |
| | Hydrogenated Polyisobutene | 3.00 |
| | TEGOSOFT ® APM (PPG-3 Myristyl Ether) | 3.00 |
| | Example 6 | 0.50 |
| | Tocopherol | 0.50 |
| B | Aqua | ad 100 |
| | Butylene Glycol | 5.00 |
| | SKINMIMICS ® (Ceteareth-25; Glycerin; Cetyl Alcohol; Behenic Acid; Cholesterol; Ceramide NP; Ceramide NS; Ceramide EOS; Ceramide EOP; Ceramide AP; Caprooyl Phytosphingosine; Caprooyl Sphingosine) | 2.50 |
| C | Polyacrylamide; C13-14 Isoparaffin; Laureth-7 (Sepigel 305, Seppic) | 0.75 |
| Z | Preservative, Perfume | q.s. |

Rich Natural Cream

| Phase | Ingredient | w/w-% | w/w-% | w/w-% | w/w-% |
|---|---|---|---|---|---|
| A | TEGO ® Care PSC 3 (Polyglyceryl-3 Dicitrate/Stearate) | 3.00 | | | |
| | Symbiomuls GC (Glyceryl Stearate Citrate; Cetearyl Alcohol; Glyceryl Caprylate) | | 3.50 | | |
| | Dermofeel NC (Polyglyceryl-3 Distearate (and) Glyceryl Stearate Citrate) | | | 2.50 | 3.00 |
| | TEGIN ® M Pellets (Glyceryl Stearate) | 0.90 | 0.30 | 0.90 | 0.50 |
| | TEGO ® Alkanol 1618 (Cetearyl Alcohol) | 0.60 | 0.30 | 0.60 | 0.60 |
| | TEGOSOFT ® P (Isopropyl Palmitate) | 3.00 | 3.00 | 3.00 | 3.00 |
| | Prunus Amygdalus Dulcis Oil | 5.00 | 5.00 | 5.00 | 5.00 |
| | TEGOSOFT ® CT (Caprylic/Capric Triglyceride) | 4.50 | 4.50 | 4.50 | 4.50 |
| | Triisostearin | 3.50 | 3.50 | 3.50 | 3.50 |
| | Example 7 | 6.00 | | 4.00 | 2.50 |
| | Example 13 | | 6.00 | 2.00 | 5.00 |
| B | Water | ad 100 | ad 100 | ad 100 | ad 100 |
| | Glycerin | 3.00 | 4.00 | 3.00 | 5.00 |
| | Xanthan Gum (Keltrol CG-SFT, CP Kelco) | 0.30 | 0.30 | 0.30 | 0.30 |
| C | Sodium hydroxide (10% in water) | q.s. | q.s. | q.s. | q.s. |
| Z | Preservative, Perfume | q.s. | q.s. | q.s. | q.s. |

After Shave Lotion

| Phase | Ingredient | w/w-% | w/w-% |
|---|---|---|---|
| A | ABIL ® Care 85 (Bis-PEG/PPG-16/16 PEG/PPG-16/16 Dimethicone; Caprylic/Capric Triglyceride) | 1.50 | |
| | ABIL ® Care XL 80 (Bis-PEG/PPG-20/5 PEG/PPG-20/5 Dimethicone (and) Methoxy PEG/PPG-25/4 Dimethicone (and) Caprylic/Capric Triglyceride) | | 1.50 |
| | TEGOSOFT ® CT (Caprylic/Capric Triglyceride) | 3.00 | 3.00 |
| | Example 8 | 3.50 | 3.50 |
| | Tocopheryl Acetate | 0.50 | 0.50 |
| | Menthyl Lactate (Frescolat ML) | 0.50 | 0.50 |
| B | TEGO ® SMO 80 V (Polysorbate 80) | 0.50 | 0.50 |
| | Aqua | ad 100 | ad 100 |
| | Glycerin | 2.00 | 2.00 |
| | Alcohol | 15.00 | 15.00 |
| C | TEGO ® Carbomer 141 (Carbomer) | 0.20 | 0.20 |
| | Xanthan Gum | 0.10 | 0.10 |
| | Mineral Oil (30 mPas) | 1.60 | 1.60 |
| D | Sodium hydroxide (10% in water) | q.s. | q.s. |
| Z | Preservative, Perfume | q.s. | q.s. |

Light W/O Emulsion

| Phase | Ingredient | w/w-% |
|---|---|---|
| A | ISOLAN ® GPS (Polyglyceryl-4 Diisostearate/Polyhydroxystearate/Sebacate) | 3.00 |
| | Example 9 | 6.40 |
| | TEGOSOFT ® DEC (Diethylhexyl Carbonate) | 6.40 |
| | Dicaprylyl Carbonate, Stearalkonium Hectorite, Propylene Carbonate (Cosmedia ® Gel CC, Cognis) | 3.00 |
| B | Water | ad 100 |
| | Glycerin | 2.00 |
| | Magnesium Sulfate Heptahydrate | 1.50 |
| C | Phenoxyethanol, Ethylhexylglycerin (euxyl ® PE 9010, Schülke & Mayr) | 0.70 |

Anti-Aging Hydration Cream

| Phase | Ingredient | w/w-% |
|---|---|---|
| A | TEGO ® Care 450 (Polyglyceryl-3 Methylglucose Distearate) | 3.00 |
| | TEGIN ® M Pellets (Glyceryl Stearate) | 2.00 |
| | TEGO ® Alkanol 18 (Stearyl Alcohol) | 1.00 |
| | TEGOSOFT ® MM (Myristyl Myristate) | 1.00 |
| | TEGOSOFT ® DO (Decyl Oleate) | 8.00 |
| | Example 14 | 11.50 |
| | Phytosphingosine SLC (Salicyloyl Phytosphingosine) | 0.10 |
| B | Glycerin | 3.00 |
| | Aqua | ad 100 |
| C | TEGO ® Carbomer 134 (Carbomer) | 0.20 |
| | TEGOSOFT ® P (Isopropyl Palmitate) | 0.80 |
| D | Sodium hydroxide (10% in water) | q.s. |
| Z | Preservative, Perfume | q.s. |

Light O/W Sun Care Lotion

| Phase | Ingredient | w/w-% |
|---|---|---|
| A | AXOL ® C 62 Pellets (Glyceryl Stearate Citrate) | 2.50 |
| | TEGO ® Alkanol 1618 (Cetearyl Alcohol) | 1.00 |
| | Example 5 | 6.00 |
| | Isoadipate (Diisopropyl Adipate) | 3.00 |

-continued

| Phase | Ingredient | w/w-% |
|---|---|---|
| | Butyloctyl Salicylate (HallBrite BHB, The HallStar Company) | 2.00 |
| | Tocopheryl Acetate | 0.20 |
| | Dimethicone (5 mPas) | 1.00 |
| | Butyl Methoxydibenzoylmethane | 1.50 |
| | Diethylamino Hydroxybenzoyl Hexyl Benzoate (Uvinul A Plus, BASF) | 4.00 |
| | Ethylhexyl Triazone | 2.00 |
| | Ethylhexyl Salicylate | 5.00 |
| | Octocrylene | 8.00 |
| | Ethylhexyl methoxycrylene | 1.50 |
| B | Titanium Dioxide; Trimethoxycaprylylsilane | 1.00 |
| C | Glycerin | 3.20 |
| | EDTA | 0.02 |
| | Water | ad 100 |
| D | Acrylates/C10-30 Alkyl Acrylate Crosspolymer | 0.10 |
| | Example 9 | 0.90 |
| E | Sodium Hydroxide (10% in water) | q.s |
| Z | Preservative, Perfume | q.s |

Sun Care Spray SPF 30

| Phase | Ingredient | w/w-% |
|---|---|---|
| A | TEGO ® Care PBS 6 MB (Polyglyceryl-6 Stearate, Polyglyceryl-6 Behenate) | 3.00 |
| | Example 2 | 3.00 |
| | Bis-ethylhexyloxyphenol Methoxyphenyl Triazine (Tinosorb S, BASF) | 3.00 |
| | Butyl Methoxydibenzoylmethane | 2.00 |
| | Homosalate | 4.00 |
| | Ethylhexyl Salicylate | 4.00 |
| | Octocrylene | 4.00 |
| | TEGO ® Feel C 10 (Cellulose) | 1.00 |
| B | Water | ad 100 |
| | Gellan Gum (Kelcogel CG-HA, CP Kelco) | 0.03 |
| | EDTA | 0.05 |
| | Glycerin | 3.00 |
| | Acrylates/C10-30 Alkyl Acrylate Crosspolymer | 0.20 |
| C | Phenylbenzimidazole Sulfonic Acid | 2.00 |
| | Tromethamine | 0.88 |
| | Water | 7.12 |
| E | Tromethamine (Trisaminomethane, 30% in water) | q.s. |
| F | dermofeel ® OMP (Methylpropanediol, Caprylyl Glycol, Phenylpropanol) | 3.00 |

Cationic Hand Cream

| Phase | Ingredient | w/w-% |
|---|---|---|
| A | VARISOFT ® TA 100 (Distearyldimonium Chloride) | 3.50 |
| | TEGIN ® M Pellets (Glyceryl Stearate) | 1.50 |
| | TEGO ® Alkanol 18 (Stearyl Alcohol) | 1.00 |
| | Example 12 | 13.00 |
| | TEGOSOFT ® DEC (Diethylhexyl Carbonate) | 8.00 |
| | TEGOSOFT ® CR (Cetyl Ricinoleate) | 1.00 |
| | Triisostearin | 1.00 |
| B | TEGO ® Cosmo C 100 (Creatine) | 0.50 |
| | Glycerin | 3.00 |
| | Water | ad 100 |
| Z | Preservative, Parfum | q.s. |

AP/Deo Roll-On, PEG- and ACH-Free

| Phase | Ingredient | w/w-% |
|---|---|---|
| A | TEGO ® Care APD 18 (Polyglyceryl-6 Stearate; Polyglyceryl-6 Behenate; C18-22 Hydroxyalkyl Hydroxypropyl Guar) | 5.00 |

-continued

| Phase | Ingredient | w/w-% |
|---|---|---|
| | Example 3 | 5.00 |
| B | Water | ad 100 |
| | Glycerin | 3.00 |
| | Potassium Alum | 5.00 |
| C | Preservative, Perfume | q.s. |

Oil Release Lotion

| Phase | Ingredient | w/w-% |
|---|---|---|
| A | TEGO ® Care PBS 6 (Polyglyceryl-6 Stearate, Polyglyceryl-6 Behenate) | 3.00 |

-continued

| Phase | Ingredient | w/w-% |
|---|---|---|
| | TEGOSOFT ® DEC (Diethylhexyl Carbonate) | 10.00 |
| | Example 8 | 26.00 |
| | TEGOSOFT ® OER (Oleyl Erucate) | 10.00 |
| | TEGOSOFT ® CT (Caprylic/Capric Triglyceride) | 15.00 |
| | TEGOSOFT ® AC (Isoamyl Cocoate) | 10.00 |
| | TEGO ® Feel C 10 (Cellulose) | 1.00 |
| B | Aqua | ad 100 |
| | Glycerin | 3.00 |
| C | Phenoxyethanol, Ethylhexylglycerin (Euxyl PE 9010, Schulke & Mayr GmbH) | 0.70 |
| D | Citric Acid (10% in water) | q.s. |

W/O Make-Up Foundation:

| | Nomenclature according to INCI | w/w-% | w/w-% | w/w-% | w/w-% | w/w-% | w/w-% |
|---|---|---|---|---|---|---|---|
| A | ISOLAN ® 17 (Polyglyceryl-4 Diisostearate/Polyhydroxystearate/ Sebacate (and) Caprylic/Capric Triglyceride (and) Polyglyceryl-3 Oleate (and) Diisostearoyl Polyglyceryl-3 Dimer Dilinoleate) | 4.00 | 3.00 | 2.00 | 3.00 | 2.00 | |
| | ISOLAN ® GPS (Polyglyceryl-4 Diisostearate/Polyhydroxystearate/Sebacate | | 1.00 | | | | |
| | Dehymuls PGPH (Polyglyceryl-2 Dipolyhydroxystearate) | | | 1.50 | | | |
| | Cithrol PG3PR (Polyglyceryl-3 Polyricinoleate) | | | | 2.00 | | |
| | ABIL ® EM 90 (Cetyl PEG/PPG-10/1 Dimethicone) | | | | | 1.50 | 3.00 |
| | Dermofeel sensolv (Isoamyl Laurate) | 7.00 | 6.00 | 5.00 | 7.00 | 2.50 | 6.00 |
| | Decyl Cocoate | 4.00 | 4.00 | | 4.00 | | 3.00 |
| | Isopropyl Myristate | 6.00 | | | 6.00 | 4.50 | |
| | Caprylic/Capric Triglyceride | | 4.00 | | | 3.00 | 4.00 |
| | Diethylhexyl Carbonate | | | 4.00 | | 5.00 | |
| | Dimethicone | | | 15.00 | | | |
| | Example 4 | 3.00 | | | 2.00 | 6.00 | 4.00 |
| | Example 11 | 2.00 | 5.00 | 5.00 | 2.00 | | 0.50 |
| | CI 77891 (and) Hydrogenated Lecithin | 5.00 | 5.00 | 5.00 | 5.00 | 5.00 | |
| | CI 77492 (and) Hydrogenated Lecithin | 0.60 | 0.60 | 0.60 | 0.60 | 0.60 | |
| | CI 77491 (and) Hydrogenated Lecithin | 0.35 | 0.35 | 0.35 | 0.35 | 0.35 | |
| | CI 77499 (and) Hydrogenated Lecithin | 0.10 | 0.10 | 0.10 | 0.10 | 0.10 | |
| | Disteardimonium Hectorite dimethicone, propylencarbonat | 2.00 | 2.00 | 2.00 | 2.00 | 2.00 | |
| B | Water | ad 100 | ad 100 | ad 100 | ad 100 | ad 100 | |
| | Sodium chloride | 1.00 | 1.00 | 1.50 | | | |
| | Magnesium Sulfate Heptahydrate | | | | 1.50 | 2.00 | |
| | Glycerin | 3.00 | 3.00 | 3.00 | 5.00 | 5.00 | |
| C | Phenoxyethanol, Caprylyl Glycol | 1.00 | 1.00 | 1.00 | 1.00 | 1.00 | |

Clear Conditioning Shampoo

| Ingredient | w/w-% |
| --- | --- |
| Example 7 | 0.1 |
| TEXAPON ® NSO, BASF, 28%-ig | 32.00 |
| (INCI: Sodium Laureth Sulfate) | |
| REWODERM ® LI S 80, Evonik Nutrition & Care GmbH | 2.00 |
| (INCI: (PEG-200 Hydrogenated Glyceryl Palmate; | |
| PEG-7 Glyceryl Cocoate) | |
| Perfume | 0.25 |
| Water | ad 100.00 |
| TEGO ® Cosmo C 100, Evonik Nutrition & Care GmbH, | 1.50 |
| (INCI: Creatine) | |
| Jaguar C-162, Solvay, (INCI: Hydroxypropyl Guar | 0.20 |
| Hydroxypropyltrimonium Chloride) | |
| TEGO ® Betain F 50, Evonik Nutrition & Care GmbH, | 8.00 |
| 38%-ig (INCI: Cocamidopropyl Betaine) | |
| NaCl | 2.50 |
| Citric Acid, 30%-ig | q.s. |
| | (pH 5.0) |
| Preservative | q.s. |

Pearlizing Shampoo

| Ingredient | w/w-% |
| --- | --- |
| TEXAPON ® NSO, BASF, 28%-ig | 32.00 |
| (INCI: Sodium Laureth Sulfate) | |
| Example 6 | 0.20 |
| Perfume | 0.15 |
| Water | ad 100.00 |
| TEGO ® Betain F 50, Evonik Nutrition & Care GmbH, 38%-ig | 8.00 |
| (INCI: Cocamidopropyl Betaine) | |
| TEGO ® Pearl N 300, Evonik Nutrition & Care GmbH, | 2.00 |
| (INCI: Glycol Distearate; Laureth-4; Cocamidopropyl Betaine) | |
| ANTIL ® 171 Evonik Nutrition & Care GmbH, | 2.50 |
| (INCI: PEG-18 Glyceryl Oleate/Cocoate) | |
| NaCl | 0.90 |
| Citric Acid, 30%-ig | q.s. (pH 5.5) |
| Preservative | q.s. |

Conditioning Shampoo

| Ingredient | w/w-% |
| --- | --- |
| TEXAPON ® NSO, BASF, 28%-ig (INCI: Sodium | 32.00 |
| Laureth Sulfate) | |
| ANTIL ® 200, Evonik Nutrition & Care GmbH, | 2.00 |
| (INCI: PEG-200 Hydrogenated Glyceryl Palmate; | |
| PEG-7 Glyceryl Cocoate) | |
| Perfume | 0.25 |
| Water | ad 100.00 |
| Polymer JR 400, Amerchol, (INCI: Polyquaternium-10) | 0.40 |
| TEGO ® Betain F 50, Evonik Nutrition & Care GmbH, | 8.00 |
| 38%-ig (INCI: Cocamidopropyl Betaine) | |
| Example 10 | 0.50 |
| TEGO ® Pearl N 300, Evonik Nutrition & Care GmbH, | 2.00 |
| (INCI: Glycol Distearate; Laureth-4; Cocamidopropyl | |
| Betaine) | |
| NaCl | 0.30 |
| Citric Acid, 30%-ig | q.s. (pH 5.5) |
| Preservative | q.s. |

Anti-Dandruff Shampoo

| Ingredient | w/w-% |
| --- | --- |
| TEXAPON ® LS 35, BASF, 30%-ig | 24.00 |
| (INCI: Sodium Lauryl Sulfate) | |
| TAGAT ® CH 40, Evonik Nutrition & Care GmbH, | 2.00 |
| (INCI: PEG-40 Hydrogenated Castor Oil) | |
| TEGOSOFT ® GC, Evonik Nutrition & Care GmbH, | 1.00 |
| (INCI: PEG-7 Glyceryl Cocoate) | |
| Example 13 | 0.15 |
| Perfume | 0.20 |
| Water | ad 100.00 |
| Polymer JR 400, Amerchol, (INCI: Polyquaternium-10) | 0.20 |
| TEGO ® Betain F 50, Evonik Nutrition & Care GmbH, | 16.00 |
| 38%-ig (INCI: Cocamidopropyl Betaine) | |
| Hostapon SG, Clariant, (INCI: Sodium Cocoyl Glycinate) | 5.00 |
| Microcare ZP, Thor, (INCI: Zinc Pyrithione) | 0.200 |
| Octopirox, Clariant, (INCI: Octopirox) | 0.10 |
| ABIL ® Quat 3272, Evonik Nutrition & Care GmbH, | 0.80 |
| (INCI: Quaternium-80) | |
| REWOMID ® D 212, Evonik Nutrition & Care GmbH, | 0.80 |
| (INCI: Cocamide MEA) | |
| ANTIL ® 500, Evonik Nutrition & Care GmbH, | 0.80 |
| (INCI: PEG-200 Glyceryl Stearate) | |
| Glycerin | 1.50 |
| NaCl | 0.90 |
| Citric Acid, 30%-ig | q.s. (pH 5.5) |
| Preservative | q.s. |

Shampoo, PEG-Free

| Ingredient | w/w-% |
| --- | --- |
| TEXAPON ® LS 35, BASF, 30% (INCI: Sodium Lauryl | 28.00 |
| Sulfate) | |
| Water | ad 100.00 |
| UCARE Polymer JR-400, Dow Chemicals, | 0.10 |
| (INCI: Polyquaternium-10) | |
| Jaguar C-162, Solvay, (INCI: Hydroxypropyl | 0.10 |
| Guar Hydroxypropyltrimonium Chloride) | |
| ANTIL ® CM 90, Evonik Nutrition & Care GmbH, | 0.50 |
| (INCI: Cocamide MEA) | |
| ANTIL ® SPA 80, Evonik Nutrition & Care GmbH, | 1.00 |
| (INCI: Isostearamide MIPA; Glyceryl Laurate) | |
| Xanthan Gum | 0.50 |
| Example 14 | 0.10 |
| Dehyton AB 30, BASF, 31%, (INCI: Coco-Betaine) | 8.00 |
| Prifrac 2920, Croda, (INCI: Lauric Acid) | 0.50 |
| TEGOSOFT ® PC 41, Evonik Nutrition & Care GmbH, | 1.00 |
| (INCI: Polyglyceryl-4 Caprate) | |
| Glycerin | 1.00 |
| Uvinul MS 40, BASF, (INCI: Benzophenon-4) | 0.10 |
| Versene 100, The Dow Chemical Company, (INCI: | 0.10 |
| Tetrasodium EDTA) | |
| Sodium Chloride | 1.00 |
| Perfume, preservative | q.s. |
| Citric Acid, 30%-ig | q.s. (pH 5.0) |

Shampoo, Sulfate-Free

| Ingredient | w/w-% |
| --- | --- |
| Bioterge AS-40 AOS, Stepan, (INCI: Sodium C14-16 | 30.00 |
| Olefin Sulfonate) | |
| Water | ad 100.00 |
| Jaguar C-162, Solvay, (INCI: Hydroxypropyl | 0.15 |
| Guar Hydroxypropyltrimonium Chloride) | |
| ANTIL ® 500 Pellets, Evonik Nutrition & Care GmbH, | 0.20 |
| (INCI: PEG-200 Glyceryl Stearate) | |
| ANTIL ® SPA 80, Evonik Nutrition & Care GmbH, | 0.50 |
| (INCI: Isostearamide MIPA; Glyceryl Laurate) | |

-continued

| Ingredient | w/w-% |
|---|---|
| Example 2 | 0.10 |
| Dehyton AB 30, BASF, 31%, (INCI: Coco-Betaine) | 8.00 |
| TAGAT ® CH 40, Evonik Nutrition & Care GmbH, (INCI: PEG-40 Hydrogenated Castor Oil) | 1.00 |
| Glycerin | 1.00 |
| Uvinul MS 40, BASF, (INCI: Benzophenon-4) | 0.10 |
| Sodium Chloride | 1.50 |
| Perfume, preservative | q.s. |
| Citric Acid, 30%-ig | q.s. (pH 5.5) |

Shampoo, Sulfat-Free

| Ingredient | w/w-% |
|---|---|
| TEGO ® Betain F 50, Evonik Nutrition & Care GmbH, 38%-ig, (INCI: Cocamidopropyl Betaine) | 22.00 |
| Water | ad 100.00 |
| Jaguar C-162, Solvay, (INCI: Hydroxypropyl Guar Hydroxypropyltrimonium Chloride) | 0.10 |
| ANTIL ® 500 Pellets, Evonik Nutrition & Care GmbH, (INCI: PEG-200 Glyceryl Stearate) | 0.30 |
| REWOPAL ® PEG 6000 DS A, Evonik Nutrition & Care GmbH, (INCI: PEG-150 Distearate) | 0.50 |
| Example 11 | 0.10 |
| Hostapon SG, Clariant, (INCI: Sodium Cocoyl Glycinate) | 10.00 |
| TEGO ® Solve 61, Evonik Nutrition & Care GmbH, (INCI: Polyglyceryl-6 Caprylate; Polyglyceryl-3 Cocoate; Polyglyceryl-4 Caprate; Polyglyceryl-6 Ricinoleate) | 1.00 |
| Glycerin | 0.50 |
| Sodium Chloride | 1.00 |
| Perfume, preservative | q.s. |
| Citric Acid, 30%-ig | q.s. (pH 4.8) |

Rinse-Off Conditioner

| Ingredient | w/w-% |
|---|---|
| Water | ad 100.00 |
| VARISOFT ® EQ 65, Evonik Nutrition & Care GmbH, (INCI: Distearoylethyl Dimonium Chloride; Cetearyl Alcohol) | 2.00 |
| VARISOFT ® BT 85, Evonik Nutrition & Care GmbH, (INCI: Behentrimonium Chloride) | 1.00 |
| Example 14 | 0.20 |
| TEGO ® Alkanol 1618, Evonik Nutrition & Care GmbH, (INCI: Cetearyl Alcohol) | 5.00 |
| Citric Acid, 30%-ig | q.s. (pH 4.0) |
| Preservative, Perfume | q.s. |

Rinse-Off Conditioner

| Ingredient | w/w-% |
|---|---|
| Water | ad 100.00 |
| TEGIN ® M Pellets, Evonik Nutrition & Care GmbH, (INCI: Glyceryl Stearate) | 1.00 |
| TEGO ® Care PSC 3, Evonik Nutrition & Care GmbH, (INCI: Polyglyceryl-3 Dicitrate/Stearate) | 0.50 |
| Jaguar C-162, Solvay, (INCI: Hydroxypropyl Guar Hydroxypropyltrimonium Chloride) | 0.10 |
| Example 6 | 1.00 |
| TEGO ® Alkanol 1618, Evonik Nutrition & Care GmbH, (INCI: Cetearyl Alcohol) | 6.00 |
| Citric Acid, 30%-ig | q.s. (pH 4.5) |
| Preservative, Perfume | q.s. |

Wet Wipes Impregnation Fluid

| Ingredient | w/w-% |
|---|---|
| Pentylene Glycol | 2.0 |
| Glycerin | 1.0 |
| TEGO ® Solve 61 (Polyglyceryl-6 Caprylate; Polyglyceryl-3 Cocoate; Polyglyceryl-4 Caprate; Polyglyceryl-6 Ricinoleate) | 2.0 |
| Example 3 | 0.5 |
| Allantoin | 0.2 |
| Maltodextrin | 0.5 |
| Chamomilla extract | 0.1 |
| Preservative | q.s. |
| Perfume | q.s. |
| Water | ad 100.0 |
| Citric Acid, 30% | ad pH 5.5 |

Wet Wipes Impregnation Fluid

| Ingredient | w/w-% |
|---|---|
| TEGO ® Solve 61 (Polyglyceryl-6 Caprylate; Polyglyceryl-3 Cocoate; Polyglyceryl-4 Caprate; Polyglyceryl-6 Ricinoleate) | 1.5 |
| TEGO ® Solve 55 (Polyglyceryl-6 Caprylate; Polyglyceryl-4 Caprate; Propylene Glycol) | 1.0 |
| Example 2 | 0.2 |
| Example 11 | 0.1 |
| Preservative | q.s. |
| Perfume | 0.1 |
| Propanediol | 3.0 |
| Water | ad 100.0 |

Cleansing Micellar Water

| Ingredient | w/w-% |
|---|---|
| Water | ad 100.0 |
| TEGOSOFT ® PC 41 (Polyglyceryl-4 Caprate) | 5.5 |
| Preservative | q.s. |
| Example 6 | 0.3 |
| Glycerin | 1.0 |
| Disodium EDTA | 0.2 |
| Citric Acid, 30% | ad pH 5.5 |

Micellar Water

| Ingredient | w/w-% |
|---|---|
| REWOTERIC ® AM C (Sodium Cocoamphopropionate) | 3.0 |
| Example 14 | 0.6 |
| TEGOSOFT ® GMC 6 (PEG-6 Caprylic/Capric Glycerides) | 5.0 |
| Water | ad 100.0 |
| Glycerin | 8.0 |
| Citric Acid | ad pH 5.5 |
| Preservative | q.s. |

The invention claimed is:

1. An aqueous composition, containing:

at least one 6-undecanol-ester, obtainable by esterification of undecan-6-ol with one selected from the group consisting of A) a monocarboxylic acid with 6 to 32 carbon atoms, and B) a polyfunctional carboxylic acid with 2 to 44 carbon atoms.

2. The aqueous composition according to claim 1, wherein the monocarboxylic acid is a fatty acid.

3. The aqueous composition according to claim 1, wherein the polyfunctional carboxylic acid is an aliphatic, linear dicarboxylic acid.

4. The aqueous composition according to claim 1, wherein the aqueous composition is a formulation.

5. The aqueous composition according to claim 1, wherein the aqueous composition contains at least one humectant.

6. A method for preparing 6-undecanol-esters, the method containing:

(a) providing ethanol and/or a lower alkanoic acid or any salts thereof, and contacting the ethanol and/or the lower alkanoic acid or any salts thereof with at least one microorganism capable of carrying out two-carbon chain elongation, to produce hexanoic acid and/or a salt thereof and/or an ester thereof;

(b) contacting the hexanoic acid and/or the salt thereof and/or the ester thereof from (a) with at least one ketonization catalyst under suitable reaction conditions for chemical ketonization of the hexanoic acid and/or the salt thereof and/or the ester thereof to 6-undecanone;

(c) contacting the 6-undecanone with at least one hydrogenation metal catalyst for catalytic hydrogenation of the 6-undecanone to 6-undecanol; and (d) esterifying the 6-undecanol with at least one selected from the group consisting of A) acyl group donors providing acyl groups of a monocarboxylic acid with 6 to 32 carbon atoms, and B) acyl group donors providing acyl groups of a polyfunctional carboxylic acid with 2 to 44 carbon atoms.

7. The method according to claim 6, wherein the at least one microorganism in (a) is selected from the group consisting of *Clostridium carboxidivorans* and *Clostridium kluyveri*.

8. The method according to claim 6, wherein the at least one ketonization catalyst of (b) is a metal oxide catalyst or a mixture thereof.

9. The method according to claim 6, wherein (b) is carried out at a temperature between 150° C. and 350° C.

10. The method according to claim 6, wherein the at least one hydrogenation metal catalyst of (c) is selected from the group consisting of ruthenium (Ru) catalysts, rhenium (Re) catalysts, nickel (Ni) catalysts, iron (Fe) catalysts, cobalt (Co) catalysts, palladium (Pd) catalysts, and platinum (Pt) catalysts.

11. The method according to claim 6, wherein the lower alkanoic acid in (a) is selected from the group consisting of acetic acid and butanoic acid.

12. The method according to claim 6, wherein the provision of the ethanol and/or the lower alkanoic acid or any salts thereof in (a) comprises synthesis of the ethanol and/or the lower alkanoic acid or any salts thereof from synthesis gas.

13. A method of preparing a cosmetic formulation, the method comprising:

mixing the aqueous composition according to claim 1 with at least one further component selected from the group consisting of humectants, UV light protection filters, and pigments.

14. A method of avoiding skin dryness, the method comprising:

spreading the aqueous composition according to claim 1 on skin.

15. The aqueous composition according to claim 1, wherein the monocarboxylic acid has 8 to 22 carbon atoms, and wherein the polyfunctional carboxylic acid is a dicarboxylic acid with 2 to 18 carbon atoms.

16. The aqueous composition according to claim 3, wherein the polyfunctional carboxylic acid is selected from the group consisting of oxalic acid, malonic acid, tartronic acid, succinic acid, maleic acid, tartaric acid, maleic acid, fumaric acid, sorbic acid, alpha-ketoglutaric acid, glutaric acid, adipic acid, pimelic acid, cork acid, azelaic acid, sebacic acid, undecane dicarboxylic acid, dodecane dicarboxylic acid, and brassylic acid.

17. The aqueous composition according to claim 4, wherein the aqueous composition is a cosmetic formulation and comprises at least one further component selected from the group consisting of humectants, UV light protection filters, and pigments.

18. The method according to claim 6, wherein in (d), the monocarboxylic acid has 8 to 22 carbon atoms, and the polyfunctional carboxylic acid is a dicarboxylic acid with 2 to 18 carbon atoms.

19. The method according to claim 8, wherein the at least one ketonization catalyst of (b) is selected from the group consisting of heteropoly acid ($H_3PW_{12}O_{40}$) catalysts, niobium oxide ($Nb_2O_5$) catalysts, titanium oxide ($TiO_2$) catalysts, cerium oxide ($Ce_{(2)}$ catalysts, zinc-chromium (Zn—Cr) mixed oxide catalysts, manganese oxide ($MnO_x$) catalysts, lanthanum oxide ($La_2O_3$) catalysts, magnesium oxide (MgO) catalysts, iron oxide (FeO, $FeO_2$, $Fe_2O_3$, $Fe_3O_4$, $Fe_4O_5$, $Fe_5O_6$, $Fe_5O_7$), silicon-aluminium ($Si_yAl_zO$) mixed oxide catalysts, aluminium oxide ($Al_2O_3$) catalysts, zirconia ($ZrO_2$) catalysts, and mixtures thereof, wherein x in $MnO_x$ is 1, 2 or 4, y and z in $Si_yAl_zO$ are any number where a ratio z/y is any number between 0 to 1.

20. The method according to claim 12, wherein the synthesis of the ethanol and/or the lower alkanoic acid or any salts thereof is by at least one acetogenic microorganism.

\* \* \* \* \*